(12) United States Patent
Marcus et al.

(10) Patent No.: US 8,058,266 B2
(45) Date of Patent: Nov. 15, 2011

(54) METHODS AND COMPOSITIONS FOR TREATMENT OF MACULAR AND RETINAL DISEASE

(75) Inventors: Dennis Michael Marcus, Martinez, GA (US); Chung Kwang Chu, Athens, GA (US)

(73) Assignee: The University of Georgia Research Foundation, Inc, Athens, GA (US)

( * ) Notice: Subject to any disclaimer, the term of this patent is extended or adjusted under 35 U.S.C. 154(b) by 794 days.

(21) Appl. No.: 11/777,825

(22) Filed: Jul. 13, 2007

(65) Prior Publication Data
US 2007/0259843 A1 Nov. 8, 2007

Related U.S. Application Data

(63) Continuation of application No. 10/639,972, filed on Aug. 13, 2003, now Pat. No. 7,259,180.

(60) Provisional application No. 60/403,499, filed on Aug. 14, 2002.

(51) Int. Cl.
*A61K 31/573* (2006.01)
*A61K 31/407* (2006.01)
*C07J 5/00* (2006.01)
*C07D 487/02* (2006.01)
*C07K 16/00* (2006.01)

(52) U.S. Cl. ........ 514/179; 514/410; 552/595; 540/469; 530/387.1; 424/1.69

(58) Field of Classification Search ................... 552/595; 540/469; 530/387.1; 424/1.69; 514/179, 514/410
See application file for complete search history.

(56) References Cited

U.S. PATENT DOCUMENTS

| 5,536,504 A | * | 7/1996 | Eugster et al. ............... 424/450 |
| 6,001,885 A | | 12/1999 | Vega et al. |
| 7,259,180 B2 | | 8/2007 | Marcus et al. |

FOREIGN PATENT DOCUMENTS

| WO | WO 91/05806 | 5/1991 |
| WO | WO 00/56367 | 9/2000 |

OTHER PUBLICATIONS

Garnett, M., "Targeted Drug Conjugates: Principles and Progress," Advanced Drug Delivery Reviews, vol. 53, No. 2, 171-216, 2001.

(Continued)

*Primary Examiner* — Barbara P Badio
(74) *Attorney, Agent, or Firm* — R. Neil Sudol; Henry D. Coleman; William J. Sapone

(57) ABSTRACT

The present invention describes linking a therapeutic agent to a compound which is known to be naturally concentrated in a tissue affected by, or that is causing, a disease, to create a prodrug for treatment of the disease. Embodiments of the present invention include a new class of carotenoid-linked drugs to treat such blinding retinal disease such as age-related macular degeneration, retinoblastoma, and diabetic macular edema. For example, the present invention comprises a method for the treatment of a disorder of the eye comprising linking a therapeutic agent to a xanthophyll carotenoid to create a prodrug, and administering a therapeutically effective amount of the prodrug to an individual in need of treatment. Provided are prodrugs for treatment of retinoblastoma, cystoid macular edema (CME), exudative age-related macular degeneration (AMD), diabetic retinopathy, diabetic macular edema, or inflammatory disorders.

22 Claims, 2 Drawing Sheets

OTHER PUBLICATIONS

Han, H.K. et al., "Targeted Prodrug Design to Optimiize Drug Delivery," AAPS Pharmsci 2000, vol. 2, No. 1, Article 6, 1-11, 2000 (http://www.pharmsci.org/).

Moeller, S. et al., "The Potential Role of Dietary Xanthophylls in Cataract and Age-Related Macular Degeneration," Journal of the American College of Nutrition, vol. 19, No. 5, 522S-527S, 2000.

Ramakrishnan, S. et al., "Targeting Tumor Vasculature Using VEGF-Toxin Conjugates," Methods in Molecular Biology, vol. 166, 219-234, 2001.

Supplementary Partial European Search Report mailed Feb. 28, 2008 corresponding to PCT/US0325229.

Aiello et al., "Vascular endothelial growth factor in ocular fluid of patients with diabetic retinopathy and other retinal disorders," *N. Engl. J. Med.*, 1994, 331: 1480-1487.

Aiello et al., "Hypoxic regulation of vascular endothelial growth factor in retinal cells," *Arch. Ophthalmol.*, 1995, 113:1538-1544.

Beatty et al., "Macular pigment and risk for age-related macular degeneration in Subjects from a Northern European population," *Invest Ophthalmol. Vis. Sci.*, 2001, 42: 439-446.

Beatty et al., The role of oxidative stress in the pathogenesis of age-related macular degeneration, *Surv. Opthalmol.*, 2000, 45: 115-134.

Berendschot et al., "Influence of lutein supplementation on macular pigment, assessed with two objective techniques," *Invest. Ophthalmol. Vis. Sci.*, 2000, 41: 3322-3326.

Bernstein et al., "Retinal tubulin binds macular carotenoids," *Invest. Ophthalmol. Vis. Sci.*, 1997, 38: 167-175.

Blair et al., "Cystoid macular edema after ocular surgery," In Albert DM, Jakobiec FA, eds. *Principles and Practice of Ophthalmology*: Philadelphia: WB Saunders, 2000, 2080-2088.

Bone et al., "Preliminary identification of the human macular pigment," *Vision Res.*, 1985, 25: 1531-1535.

Bone et al., "Stereochemistry of the human macular carotenoids," *Invest. Ophthalmol. Vis. Sci.*, 1993, 34: 2033-2040.

Bone et al., "Distribution of lutein and zeaxanthin stereoisomers in the human retina," *Acad. Press.*, 1997, 44: 211-218.

Bone et al., "Lutein and zeaxanthin in the eyes, serum and diet of human subjects," *Experimental Eye Research*, 2000, 71: 239-245.

Cooperwood et al., "Nucleoside and nucleotide prodrugs," In: *Recent Advances in Nucleosides: Chemistry and Chemotheraphy*, CK Chu, ed. 2002, 91-147.

Doft, "The endophthalmitis vitrectomy study," *Arch. Ophthalmol.*, 1991, 109: 487-488.

Flach et al., "Improvement in visual acuity in chronic aphakic and pseudophakic cystoid macular edema after treatment with topical 0.5% ketorolac tromethamine," *Am. J. Opthalmol.*, 1991, 112: 514-519.

Flach et al., "Effectiveness of ketorolac tromethamine 0.5% ophthalmic solution for chronic aphakic and pseudophakic cystoid macular edema," *Am. J. Ophthalmol.*, 1987, 103: 479-486.

Fung, "Vitrectomy for chronic aphakic cystoid macular adema. Results of a national collaborative, prospective, randomized investigation," *Ophthalmology*, 1985, 92: 1102-1111.

Goodwin, "Metabolism, nutrition, and function of carotenoids," *Ann. Rev. Nutr.*, 1986, 6: 273-297.

Guex-Crosier, "The pathogenesis and clinical presentation of macular edema in inflammatory diseases," *Doc. Ophthalmol.*, 1999, 97: 93-105. (93-105).

Hammond et al., "Iris color and macular pigment optical density," *Exp. Eye Res.*, 1996, 62: 293-297.

Hammond et al., "Dietary modification of human macular pigment density," *Invest. Ophthalmol. Vis. Sci.*, 1997, 38: 1795-1801.

Jampol et al., "Antioxidants and zinc to prevent progression of age-related macular degeneration," *JAMA*, 2001, 286(19): 2466-2468.

Johnson et al., "Relation among serum and tissue concentrations of lutein and zeaxanthin and macular pigment density," *Am. J. Clin. Nutr.*, 2000, 71: 1555-1562.

Kaplan et al., "Carotenoid composition, concentrations, and relationships in various human organs," *Chin. Physiol. Biochem.*, 1990, 8: 1-10.

Kliffen et al., Increased expression of angiogenic growth factors in age-related maculopathy, *Br. J. Ophthalmol.*, 1997, 81: 154-162.

Landrum et al, "A one year study of the macular pigment: The effect of 140 days of a lutein supplement," *Exp. Eye Res.*, 1997, 65: 57-62.

Landrum et al., "The macular pigment: a possible role in protection from age-related macular degeneration," *Adv. Pharmacol.*, 1997, 38: 537-556.

Leung et al., "Absorption and tissue distribution of zeaxanthin and lutein in rhesus monkeys after taking fructus lycii (Gou Qi Zi) Extract," *Invest. Ophthalmol. Vis. Sci.*, 2001, 42: 466-471.

Lumbroso et al., "Chemothermotherapy in the management of retinoblastoma," *Ophthalmology*, 2002, 109: 1130-1136.

Marcus, D. et al., "Carotenoid-Mediated Delivery of Ketorolac and Triamcinolone," Invest. Ophthalmol. Vis. Sci., 47: Abstract #3803, 2006. Also presented at Annual Meeting of Association for Research in Opthalmology, Ft. Lauderdale, Florida, May 2006, Retina Society Meeting, San Diego, CA, Sep. 2005, and Macula Society Meeting, San Diego, CA, Feb. 2006.

Marcus, D. et al., "Carotenoid-Mediated Delivery of Ketorolac and Triamcinolone," Department of Ophthalmology, University of South Carolina, Columbia, SC. Poster Presented at Annual Meeting of Association for Research in Ophthalmology, Ft. Lauderdale, Florida May 2006, and Retina Society Meeting, San Diego, CA Sep. 2005.

Mares-Perlman et al., "Lutein and zeaxanthin in the diet and serum and their relation to age-related maculopathy in the third national health and nutrition examination survey," *Am. J. Epidemiol.*, 2001, 153: 424-432.

Pendergast et al., "Vitrectomy for chronic pseudophakic cystoid macular edema," *Am. J. Ophthalmol.*, 1999, 128: 317-323.

Pratt, "Dietary prevention of age-related macular degeneration," *J. Am. Optom. Assoc.*, 1999, 70: 39-47.

Schalch, "Carotenoids in the retina—a review of their possible role in preventing or limiting damage caused by light and oxygen," *Free Radicals and Aging*, 1992, 280-298.

Seddon et al., "Dietary carotenoids, vitamins A, C, and E and advanced age-related macular degeneration," *JAMA*, 1994, 272: 1413-1420.

Sec et al., "Dramatic inhibition of retinal and choroidal neovascularization by oral administration of a kinase inhibitor," *Amer. J. Pathology*, 1999, 154: 1743-1753.

Shin et al., "Role of protein kinase C isoforms in phorbol ester-induced vascular endothelial growth factor expression in human glioblastoma cells," *J. Biol. Chem.*, 1999, 274(22): 15407-15414.

Sommerburg et al., "Fruits and vegetables that are sources for lutein and zeaxanthin: the macular pigment in human eyes," *Br. J. Ophthalmol.*, 1998, 82: 907-910.

Snodderly, "Evidence for protection against age-related macular degeneration by carotenoids and antioxidant vitamins," *Am J. Clin. Nutr.*, 1995, 62(Supp 6): 1448S-1461S.

Sujak et al., "Lutein and zeaxanthin as protectors of lipid membranes against oxidative damage: the structural aspects," *Arch. Biochem and Biophys.*, 1999, 371: 301-307.

Toyoda et al., "Effect of dietary zeaxanthin on tissue distribution of zeaxanthin and lutein in Quail," Invest *Ophthalmol. Vis. Sci*, 2002, 43: 1210-1221.

Yoshiji, "Protein kinase C lies on the signaling pathway for vascular endothelial growth factor-mediated tumor development and angiogenesis," *Cancer Res.*, 1999, 59: 4413-4418.

www.eyetk.com, Lead compound, Aptamers, *Eye Tech Pharmaceuticals*, 3 pages, 2003.

www.macular.org, Genentech announces preliminary positive phase Ib/II data for rhuFab V2 in age-related macular degeneration (AMD), 3 pages, 2003.

International Search Report mailed Jul. 29, 2004 corresponding to PCT/US03/25229.

Notice of Allowance and Fees due mailed Apr. 17, 2007 for U.S. Appl. No. 10/639,972.

Office Action Summary mailed Oct. 27, 2006 for U.S. Appl. No. 10/639,972.
Office Action Summary mailed Jul. 6, 2006 for U.S. Appl. No. 10/639,972.
Amendment and Response to Non-Final Office Action mailed to USPTO on Jan. 29, 2007 for U.S. Appl. No. 10/639,972.
Election and Response mailed to USPTO on Aug. 7, 2006 for U.S. Appl. No. 10/639,972.
Interview Summary mailed Apr. 17, 2007 for U.S. Appl. No. 10/639,972.

* cited by examiner

X-OH = Xanthophyll

METHODS AND COMPOSITIONS FOR TREATMENT OF MACULAR AND RETINAL DISEASE

RELATED APPLICATIONS

This application claims priority to provisional application Ser. No. 60/403,499, filed Aug. 14, 2002, and is a continuation application of non-provisional application Ser. No. 10/639,972, filed Aug. 13, 2003, now U.S. Pat. No. 7,259,180. The entire disclosures of provisional application 60/403,499 and nonprovisional application Ser. No. 10/639,972 are incorporated in its entirety herein.

FIELD OF THE INVENTION

The present invention relates to methods and compositions for treatment and prevention of disease, and in particular embodiments, disorders of the eye. In an embodiment, the present invention describes linking therapeutic compounds to xanthophyll carotenoids to enhance accumulation of the therapeutic compound in the retina and macula of the eye.

BACKGROUND OF THE INVENTION

The retina is the part of the eye that is sensitive to light. The macula lutea is the region of the retina that allows us to read and recognize faces. Diseases of the macula, such as age-related macular degeneration and diabetic macular edema, account for a major proportion of legal blindness. To combat these diseases, a variety of accepted and experimental medications are employed via systemic routes or local, invasive surgical procedures.

A remarkable increase in knowledge and interest surrounding the pharmacologic treatment of macular and retinal diseases has occurred. As a result, a variety of promising agents are now being investigated for their effects on such blinding disorders as exudative age-related macular degeneration, diabetic retinopathy, macular edema, retinoblastoma, and other diseases of the retina and macula lutea. Currently, these drugs are delivered to the macula and retina via local, invasive surgical procedures, such as intravitreal or periorbital injections, or via systemic routes. Surgical methods often require repeated injections and may lead to serious ocular complications, including endophthalmitis, retinal detachment, and vitreous hemorrhage. Likewise, systemic administration is associated with a variety of potential systemic side effects and with the difficulty of delivering therapeutic levels of the drugs to the retina.

Given the recent advances in developing pharmacologic treatments for a variety of macular and retinal diseases, improving drug targeting and delivery are of paramount importance. For example, retinoblastoma, a neoplastic process that arises from the retina, is the most common primary ocular cancer of childhood. Though once treated almost exclusively with radiation or eye removal (enucleation), systemic chemotherapy is now the sight and lifesaving therapy of choice. In addition, various anti-inflammatory and anti-angiogenic agents are being investigated for use in treating exudative age-related macular degeneration (AMD) (the leading cause of legal blindness in the elderly) and for diabetic retinopathy (the leading cause of blindness in working Americans). In order to advance the noninvasive, pharmacologic treatment of retinoblastoma and other retinal diseases, new drugs having improved delivery to the retina are needed.

SUMMARY

To advance the noninvasive, pharmacologic treatment of macular degeneration, diabetic retinopathy, and other retinal diseases, the present invention describes the synthesis of a new class of drugs comprising a therapeutic agent known to be effective against a particular eye disorder chemically linked to a carotenoid. Since the macula preferentially concentrates xanthophyll carotenoids within its layers, xanthophyll carotenoids provide an ideal carrier for drug delivery to the macula. In an embodiment, enhanced accumulation of therapeutic medications using the conjugates of the present invention constitutes an improvement in drug efficacy over that achieved by current routes of administration and to overall improved treatment of macular diseases.

Thus, in an embodiment, the present invention comprises a compound for the treatment of an eye disorder comprising a therapeutic agent linked to a carotenoid. In an embodiment, the carotenoid comprises a xanthophyll carotenoid.

In another embodiment, the present invention comprises composition for the treatment of an eye disorder comprising a pharmaceutically effective amount of a prodrug comprising a therapeutic agent linked to a carotenoid, and a pharmaceutically acceptable carrier, wherein a pharmaceutically effective amount of the prodrug comprises an amount sufficient to ameliorate, prevent, or cure the eye disorder.

In yet another embodiment, the present invention describes a method for the treatment of a disorder of the eye comprising linking a therapeutic agent to a carotenoid to create a prodrug, and administering a pharmaceutically effective amount of the prodrug to an individual in need of treatment, wherein a pharmaceutically effective amount of the prodrug comprises an amount sufficient to ameliorate, prevent or cure said eye disorder.

In yet another embodiment, the present invention comprises a kit for the treatment of an eye disorder comprising:

(a) a prodrug compound comprising a therapeutic agent linked to a carotenoid;

(b) a pharmaceutically acceptable carrier; and (c) instructions to dispense a pharmaceutically effective amount of the prodrug mixed with the pharmaceutically acceptable carrier to an individual in need thereof, wherein a pharmaceutically effective amount of the prodrug comprises an amount sufficient to ameliorate, prevent, or cure an eye disorder in the individual.

In an embodiment, the methods and compounds of the present invention may also used to treat diseases of other tissues known to concentrate carotenoids. For example, the compounds may also be used to treat diseases of the liver or fat tissue.

Thus, in another embodiment, the present invention comprises a compound for the treatment of a disorder in a tissue type that is known to concentrate carotenoids, comprising a therapeutic agent linked to a carotenoid.

In yet another embodiment, the present invention comprises a method for the treatment of a disease comprising linking a therapeutic agent to a compound which is known to be naturally concentrated in a tissue affected by, or that is causing, the disease to create a prodrug, and administering a pharmaceutically effective amount of the prodrug to an individual in need of treatment, wherein a pharmaceutically effective amount of the prodrug comprises an amount sufficient to ameliorate, prevent, or cure the disease.

For example, the present invention includes the synthesis of compounds having a xanthophyll carotenoid linked to therapeutic agents including, but not limited to, non-steroidal anti-inflammatory drugs (NSAIDs), steroids, anti-angiogenic drugs, anti-neoplastic agents, and drugs to prevent infectious disease (antiviral agents, antibacterial agents, anti-protozoan agents).

Thus, embodiments of the present invention describe the use of compounds which are naturally concentrated in the macula and retina to deliver therapeutic agents to these regions of the eye. Advantages associated with embodiments of the present invention include enhanced targeting of various therapeutic medications through noninvasive means. Thus, one advantage associated with embodiments of the present invention includes increased specificity and efficacy of drug treatment. Yet another advantage associated with embodiments of the present invention is that the treatment results in fewer side effects and complications of due to the targeted nature of the delivery system. Yet another advantage associated with embodiments of the present invention is the ability to employ systemic drug administration, as opposed to local, invasive surgical procedures.

From the foregoing summary, it is apparent that an object of the present invention is to develop methods and compositions that will be effective in targeting therapeutic agents to treat diseases of specific tissue types or organs. It is to be understood that the invention is not limited in its application to the specific details as set forth in the following description and figures. The invention is capable of other embodiments and of being practiced or carried out in various ways.

DETAILED DESCRIPTION

Figure 1A:
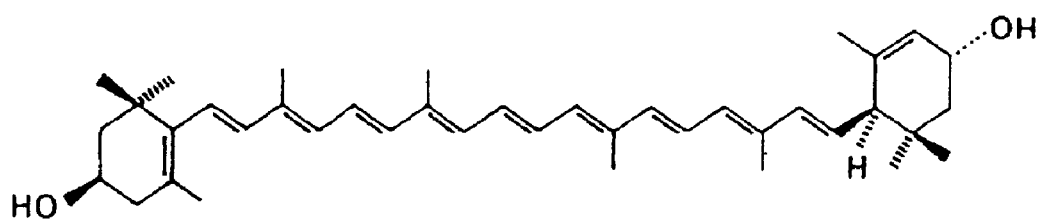
FIG. 1 shows the chemical structures of (3R,3'R,6'R)-lutein (Panel A), and (3R,3'R)-zeaxanthin (Panel B), which in accordance with an embodiment of the present invention, comprise xanthophyll carotenoids that may be linked to therapeutic agents to promote uptake of the therapeutic agent in the eye.

The present invention describes a new class of xanthophyll-linked drugs that effectively treat such blinding retinal diseases as age-related macular degeneration, retinoblastoma, diabetic macular edema and retinopathy. With advances in pharmacologic interventions for these diseases, the xanthophyll-mediated drug delivery system of the present invention provides ocular specificity and minimal systemic side effects.

Thus, in one embodiment, the present invention comprises a compound for the treatment of an eye disorder comprising a therapeutic agent linked to a carotenoid. In an embodiment, the carotenoid comprises a xanthophyll carotenoid.

As used herein, a therapeutic agent is a compound that has the ability to ameliorate, prevent, or cure a particular disease. Also as used herein, a carotenoids are lipophilic pigments having absorption peaks ranging from 450-480 nm, and that are red, orange or yellow in color. Carotenoids include carotenes and xanthophylls. Also as used herein, a carotene comprises a hydrocarbon carotenoid, and a xanthophyll comprises an oxygenated carotene.

In another embodiment, the present invention comprises a composition for the treatment of an eye disorder comprising a pharmaceutically effective amount of a prodrug comprising a therapeutic agent linked to a carotenoid, and a pharmaceutically acceptable carrier, wherein a pharmaceutically effective amount of the prodrug comprises an amount sufficient to ameliorate, prevent, or cure the eye disorder. In an embodiment, the carotenoid comprises a xanthophyll carotenoid.

Preferably, the carotenoid of the compounds and the compositions of the present invention acts as a carrier to facilitate systemic delivery of the therapeutic agent to the retina and/or the macula. As used herein, a carrier is a compound that facilitates delivery of a particular agent (e.g., a therapeutic drug) to the target area or tissue of interest. A carrier may be covalently linked to the agent, as in the case of a carotenoid carrier which is linked to the therapeutic compound. Alternatively, the agent may be physically mixed with, or dissolved in, the carrier, as in the case where prodrugs of the present invention are dissolved in a physiological carrier (such as saline) for systemic injection.

In an embodiment, the xanthophyll carotenoid comprises zeaxanthin. Alternatively, the xanthophyll may comprise lutein. Other xanthophylls known in the art, such as oxidation products of lutein and zeaxanthin, may be used. Thus, other xanthophyll compounds that may be used include, but are not limited to, 3'-epilutein, meso-zeaxanthin, 3-hydroxy-beta, epsilon-caroten-3'-one, epsilon-lycopenes, or 5-Z-lycopenes.

In an embodiment, the therapeutic agent used for the compounds and the compositions of the present invention comprises an anti-angiogenic agent. As used herein, an anti-angiogenic agent comprises an agent that ameliorates or prevents vascularization of a tissue by the development of new capillary blood vessels. Preferably, the anti-angiogenic agent comprises anecortave acetate, anti-VEGF aptamer (and other anti-VEGF agents), AMD-FAB, or protein kinase c inhibitor. Other anti-angiogenic agents known in the art may be used. Thus, other anti-angiogenic agents that may be used include, but are not limited to, steroids and angiostatic steroids, metalloproteinase inhibitors, and interferons.

Also, the therapeutic agent may comprise an anti-neoplastic agent. As used herein, an anti-neoplastic agent comprises a compound that may be used to retard tumor or endothelial cell formation, growth, or spread. Preferably, the anti-neoplastic agent comprises etoposide or vincristine, which are anti-neoplastic agents used to treat retinoblastoma. Other anti-neoplastic agents known in the art may also be used.

In yet another embodiment, the therapeutic agent used for the compounds and the compositions of the present invention comprises an anti-inflammatory agent. Preferably, the anti-inflammatory agent comprises a steroid or a non-steroidal anti-inflammatory drug (NSAID). More preferably, the anti-inflammatory agent comprises ketorolac, triamcinolone or fluocinolone. Other anti-inflammatory agents known to be effective in treating eye disease may be also be used. Thus, other anti-inflammatory agents that may be used include, but are not limited to, other steroids, interleukins, anti-leukotriene agents, cyclooxygenase inhibitors, and prostaglandin inhibitors.

In yet another embodiment, the therapeutic agent of the compounds and the compositions of the present invention comprises agents to prevent infectious disease. In an embodiment, the therapeutic agent comprises an antibiotic. Preferably, the antibiotic comprises ciprofloxacin. Other therapeutic agents known in the art to be effective against infectious pathogens may also be used. Thus, other anti-infectious agents that may be used include, but are not limited to, anti-viral agents, anti-fungal agents, and compounds known to prevent infection of the eye by other microorganisms, such as protozoa, and the like.

In an embodiment, the therapeutic agent of the compounds and the compositions of the present invention is known to be effective for treatment of macular or retinal disease. For example, the therapeutic agent may comprise a compound used to treat retinoblastoma. In another embodiment, the therapeutic agent comprises a compound used to treat cystoid macular edema (CME). Alternatively and/or additionally, the therapeutic agent may be a compound effective for treatment of exudative age-related macular degeneration (AMD). In another embodiment, the therapeutic agent is used to treat diabetic retinopathy. Still in another embodiment, the therapeutic agent may be effective for treatment of diabetic macular edema. The therapeutic agent may also be used to treat inflammatory disorders of the eye, such as CME or posterior uveitis.

Preferably, the prodrug of the compounds and the compositions of the present invention facilitates delivery of the therapeutic agent to the macula. Once in the macula, the therapeutic agent must be released from the carotenoid carrier for uptake and delivery into the cell. Thus, in an embodiment, the linkage between the therapeutic agent and the carotenoid carrier comprises a biologically cleavable bond.

In an embodiment, the therapeutic agent is directly linked to the carotenoid to form a bipartate structure. In the bipartate approach, a drug is linked directly to a carrier molecule through a chemical bond. For example, in an embodiment, the linkage between the therapeutic agent and the carotenoid carrier comprises an ester bond formed by condensation (with loss of water) of a xanthophyll and the drug to form a bipartate compound. Depending upon the active group in the therapeutic agent, other direct bonds (e.g., carbon-carbon bonds; carbonate bonds, ether linkages) may be formed.

Alternatively, a spacer molecule is used to link the therapeutic agent to a carotenoid carrier to form a tripartate structure. In the tripartate approach, the drug is linked to a spacer, which in turn is linked to a carrier molecule. The spacer can be used to connect two molecules that cannot be connected directly for chemical (e.g., reactivity of active groups) or physical (e.g., steric hindrance) reasons. The spacer may be used to modify the chemical and/or physical properties of the system (e.g., solubility, chemical stability, enzymatic stability), or to add new properties to the system (e.g., susceptibility to metabolism by a different enzyme). The tripartate approach, however, may require that two bonds are cleaved to release the drug.

For example, the linkage between the therapeutic agent and the carotenod may comprise an amino acid spacer to form a tripartate compound. In an embodiment, the linkage between the therapeutic agent and the carotenoid may comprise a dicarboxylic amino acid spacer. The linkage between the therapeutic agent and the carotenod may also comprise a carbonate spacer. Thus, to form a tripartate compound, bonds linking the therapeutic agent to the xanthopyll may comprise a carbonate bond, an ester bond, or an amide bond.

In another embodiment, the present invention comprises a method for the treatment of a disorder of the eye comprising linking a therapeutic agent to a carotenoid to create a prodrug, and administering a pharmaceutically effective amount of the prodrug to an individual in need of treatment, wherein a pharmaceutically effective amount of the prodrug comprises an amount sufficient to ameliorate, prevent, or cure the eye disorder. In an embodiment, the carotenoid comprises a xanthophyll carotenoid.

Preferably, the carotenoid acts as a carrier to facilitate delivery of the therapeutic agent to the retina and or the macula. In an embodiment of the method, the xanthophyll comprises lutein. Alternatively, the xanthophyll may comprise zeaxanthin. Other xanthophylls known in the art, such as oxidation products of lutein and zeaxanthin, may be used.

Thus, other xanthophyll compounds that may be used include, but are not limited to, 3'-epilutein, meso-zeaxanthin, 3-hydroxy-beta, epsilon-caroten-3'-one, epsilon-lycopenes, or 5-Z-lycopenes.

In an embodiment of the methods of the present invention, the therapeutic agent comprises an anti-angiogenic agent. Preferably, the anti-angiogenic agent comprises anecortave acetate, anti-VEGF aptamer, AMD-FAB, or protein kinase c inhibitor. Other anti-angiogenic agents known in the art may be used. Thus, other anti-angiogenic agents that may be used include, but are not limited to, steroids and angiostatic steroids, metalloproteinase inhibitors, and interferons.

In another embodiment of the methods of the present invention, the therapeutic agent comprises an anti-neoplastic agent. Preferably, the anti-neoplastic agent comprises etoposide or vincristine, which are anti-neoplastic agents used to treat retinoblastoma. Other anti-neoplastic agents known in the art may also be used.

In yet another embodiment of the methods of the present invention, the therapeutic agent comprises an anti-inflammatory agent. Preferably, the anti-inflammatory agent comprises a steroid or a non-steroidal anti-inflammatory drug (NSAID). More preferably, the anti-inflammatory agent comprises ketorolac, triamcinolone or fluocinolone. Other anti-inflammatory agents known to be effective for treating inflammation of the eye may be also be used. Thus, other anti-inflammatory agents that may be used include, but are not limited to, interleukins, anti-leukotriene agents, cyclooxygenase inhibitors, and prostaglandin inhibitors.

In yet another embodiment, the therapeutic agent comprises an antibiotic. Preferably, the antibiotic comprises ciprofloxacin. Other therapeutic agents known in the art to be effective against infectious pathogens may also be used. Thus, other therapeutic agents that may be used include, but are not limited to, antiviral agents and agents to prevent infection of the eye by protozoa, fungi or other microorganisms.

In an embodiment of the method, the therapeutic agent is known to be effective for treatment of macular or retinal disease. For example, the therapeutic agent may comprise a compound used to treat retinoblastoma. In another embodiment, the therapeutic agent comprises a compound used to treat cystoid macular edema (CME). Alternatively and/or additionally, the therapeutic agent may be a compound effective for treatment of exudative age-related macular degeneration (AMD). In another embodiment, the therapeutic agent is used to treat diabetic retinopathy. Still in another embodiment, the therapeutic agent may be effective for treatment of diabetic macular edema. The therapeutic agent may also be a compound used to treat inflammatory disorders of the eye, such as CME or posterior uveitis.

Preferably, the prodrug facilitates delivery of the therapeutic agent to the macula. Once in the macula, the therapeutic agent must be released from the carotenoid carrier for uptake and delivery into the cell. Thus, in an embodiment of the method, the linkage between the therapeutic agent and the carotenoid carrier comprises a biologically cleavable bond.

In an embodiment of the method, the therapeutic agent is directly linked to a carotenoid to form a bipartate structure. In the bipartate approach, a drug is linked directly to a carrier molecule through a chemical bond. For example, in an embodiment, the linkage between the therapeutic agent and the carotenoid carrier comprises an ester bond formed by condensation (with the loss of water) of a xanthophyll and the drug to form a bipartate compound. Depending upon the active group in the therapeutic agent, other direct bonds (e.g., carbon-carbon bonds; carbonate bonds, ether linkages) may be formed.

Alternatively, a spacer molecule is used to link the therapeutic agent to a carotenoid to form a tripartate structure. In the tripartate approach, the drug is linked to a spacer, which in turn is linked to a carrier molecule. The spacer can be used to connect two molecules that cannot be connected directly for chemical (e.g., reactivity of active groups) or physical (e.g., steric hindrance) reasons. The spacer may be used to modify the chemical and/or physical properties of the system (e.g., solubility, chemical stability, enzymatic stability), or to add new properties to the system (e.g., susceptibility to metabolism by a different enzyme). The tripartate approach, however, may require that two bonds are cleaved to release the drug.

For example, the linkage between the therapeutic agent and the carotenoid may comprise an amino acid spacer to form a tripartate compound. In an embodiment, the linkage between the therapeutic agent and the carotenoid may comprise a dicarboxylic amino acid spacer. The linkage between the therapeutic agent and the carotenoid may also comprise a carbonate spacer. Thus, to form a tripartate compound, bonds linking the therapeutic agent to the xanthopyll may comprise a carbonate bond, an ester bond, or an amide bond.

Preferably, the prodrugs of the present invention may be administered by a variety of routes. For example, the prodrug may be administered systemically. Thus, in an embodiment, administration is intravenous. Alternatively, administration may be intramuscular. In another embodiment, administration is subcutaneous. In yet another embodiment, the drug is administered topically, to the surface of the eye. In yet another embodiment, administration is oral. Also, in an embodiment, administration of the prodrugs of the present invention may comprise altering of the diet to increase uptake of the prodrug.

Preferably, the compounds, compositions, and methods of the present invention allow for increased uptake of the therapeutic agent in the eye as compared to uptake of the therapeutic agent when the carotenoid carrier is not used. Thus, the doses for each prodrug may depend upon the nature of the therapeutic agent, as well as the nature of the carotenoid carrier. In an embodiment, the prodrug is administered in a dosage amount that ranges from 50 mg/kg q.d. (i.e., per day) to 0.01 mg/kg q.d. In another embodiment, the prodrug is administered in a dosage amount that ranges from 5 mg/kg q.d. to 0.1 mg/kg q.d.

In yet another embodiment, the present invention comprises a kit for the treatment of an eye disorder comprising:

(a) a prodrug compound comprising a therapeutic agent linked to a carotenoid;

(b) a pharmaceutically acceptable carrier, and (c) instructions to dispense a pharmaceutically effective amount of the prodrug in the pharmaceutically acceptable carrier to an individual in need thereof, wherein a pharmaceutically effective amount of the prodrug comprises an amount sufficient to ameliorate, prevent, or cure an eye disorder in the individual. In an embodiment, the carotenoid comprises a xanthophyll carotenoid.

In an embodiment, the methods and compounds of the present invention may also used to treat diseases of other tissues known to concentrate carotenoids. For example, the compounds may also be used to treat diseases of the liver or fat tissue.

Thus, in another embodiment, the present invention comprises a compound for the treatment of a disorder in a tissue type that is known to concentrate carotenoids, comprising a therapeutic agent linked to a carotenoid. In an embodiment, the carotenoid comprises a xanthophyll. Also in an embodiment, the tissue treated comprises eye tissue, liver tissue, or fat tissue. The therapeutic agent may be almost any agent that is used to treat the disease or disorder in question and that can be linked to a carotenoid carrier. Thus, in an embodiment, the therapeutic agent comprises an anti-angiogenic agent, an anti-neoplastic agent, an anti-inflammatory agent, a non-steroidal anti-inflammatory drug (NSAID), a steroid, an antibiotic, an anti-protozoan agent, or an antiviral agent.

In yet another embodiment, the present invention comprises a method for the treatment of a disease comprising linking a therapeutic agent to a compound which is known to be naturally concentrated in a tissue affected by, or that is causing, the disease to create a prodrug, and administering a pharmaceutically effective amount of the prodrug to an individual in need of treatment, wherein a pharmaceutically effective amount of the prodrug comprises an amount sufficient to ameliorate, prevent, or cure the disease.

In an embodiment, the compound which is naturally concentrated in the tissue affected by, or that is causing, the disease comprises a carotenoid. Preferably, the carotenoid comprises a xanthophyll. Also in an embodiment, the tissue treated comprises eye tissue, liver tissue, or fat tissue. The therapeutic agent may be almost any agent that is used to treat the disease or disorder in question and that can be linked to the selected carrier (e.g., a carotenoid). Thus, in an embodiment, the therapeutic agent comprises an anti-angiogenic agent, an anti-neoplastic agent, an anti-inflammatory agent, a non-steroidal anti-inflammatory drug (NSAID), a steroid, an antibiotic, an anti-protozoan agent, or an antiviral agent.

Thus, embodiments of the present invention utilize the ability of tissues, such as the retina and the macula, to concentrate carotenoids as a means to enhance accumulation of therapeutic drugs in the that tissue. Lutein and zeaxanthin are members of the xanthophyll carotenoid family of compounds, which are characterized by a $C_{40}H_{56}$ isoprenoid backbone. Carotenoids are synthesized by plants and microorganisms, in which they have pigmentation and photoprotective roles. Humans have a limited ability to synthesize carotenoids and thus, obtain approximately 40 of these compounds from dietary sources and incorporate them into tissues, including serum, liver, and fat.

Figure 1B:
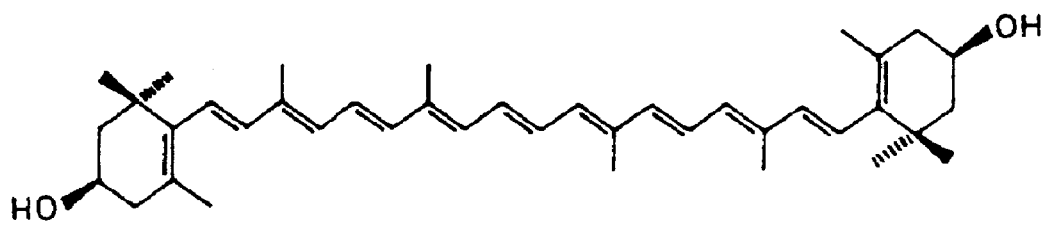

When carotenoids contain one or more oxygen atoms, as in lutein and zeaxanthin, they are known as xanthophylls. Lutein is relatively abundant in the human diet, and is derived from such dark green, leafy vegetables as spinach, kale, and broccoli. Zeaxanthin, found at lower blood levels, is derived from corn, peaches, citrus fruits and melons (Goodwin, T. W., *Ann. Rev. Nutr.*, 1986, 6:273-97; Sommerburg, O., et al., *Br. J. Ophthalmol.*, 1998, 82:907-910; Bone, R. A., et al., *Academic Press*, 2000, 43:239-245; Bone, R. A., et al., *Invest. Ophthalmol. Vis. Sci.*, 1993, 34:2033-2040; Toyoda, Y., et al., *Invest. Ophthalmol. Vis. Sci.*, 2002, 43:1210-1221). FIG. 1 displays the chemical structures of lutein (Panel A) and zeaxanthin (Panel B).

The yellow coloration of the human macula, which is the central region of the retina used for fine, detailed vision, is derived from a mixture of lutein and zeaxanthin (Bone, R. A., et al., *Vision Res.*, 1985, 25:1531-1535; Bone, R. A., et al., *Acad. Press*, 1997, 44:211-218). Since xanthophylls display anti-oxidant properties in vitro, they are hypothesized to scavenge free radicals and absorb short-wavelength light within the eye, preventing oxidative tissue injury (Sujak, A., et al., *Arch. Biochem. and Biophys.*, 1999; 371:301-307; Schalch, W. In *Free Radicals and Aging*, 1992, pp. 280-298; Beatty, S., et al., *Surv. Opthalmol.*, 2000, 45:115-134).

Interestingly, it has been reported that individuals with a high dietary intake of lutein and zeaxanthin have lower rates of age-related macular degeneration (AMD), the leading cause of legal blindness in the elderly (Bone, R. A., et al., *Academic Press*, 2000, 43:239-245; Beatty, S., *Invest. Ophthalmol. Vis. Sci.*, 2001, 42: 439-446; Snodderly, D. M., *Am. J. Clin. Nutr.*, 1995, 62 (suppl.):1448S-61S; Mares-Perlman, J. A., et al., *Am. J. Epidemiol.*, 2001, 153:424-32; Seddon, J. M., et al., *JAMA*, 1994, 272:1413-1420; Landrum, J. T., et al., *Adv. Pharmacol.*, 1997, 38:537-56). In response, lutein and zeaxanthin supplementation has been proposed as an untested treatment for AMD, resulting in heavy marketing by the vitamin and nutrition supplement industry (Pratt, S., *J. Am. Optom. Assoc.*, 1999, 70:39-47; Sommerburg, O., et al., *Br. J. Ophthalmol.*, 1998, 82:907-910; Jampol, L. M., et al., *JAMA*, 2001, 286:2466-2468). Also, oral supplementation of dietary xanthophyll sources has been experimentally shown to increase the concentration of macular pigment, though the precise mechanism for this accumulation remains elusive (Toyoda, Y., et al., *Invest. Ophthalmol. Vis. Sci.*, 2002, 43:1210-1221; Hammond, B. R., et al. *Exp. Eye Res.*, 1996, 62:293-297; Landrum, J. T., et al., *Exp. Eye Res.*, 1997, 64:311-316; Hammond, B. R., et al., *Invest. Ophthalmol. Vis. Sci.*, 1997, 38:1795-1801; Berendschot, Tos T. J. M., et al., *Invest. Ophthalmol. Vis. Sci.*, 2000, 41:3322-3326; Bernstein, P. S., et al. *Invest. Ophthalmol. Vis. Sci.*, 1997, 38:167-175; Leung, I. Y. F., et al., *Invest. Ophthalmol. Vis. Sci.*, 2001, 42: 466-471).

Thus, although the precise mechanism for xanthophyll accumulation in the retina remains obscure, there is evidence that xanthophyll compounds may be accumulated in the macula region of the eye. Embodiments of the present invention use xanthophyll carotenoids, such as lutein and zeaxanthin, as carrier molecules for medications currently used in the treatment of diseases of the eye to promote delivery and accumulation of the medication in the eye. By chemically bonding the xanthophyll carrier to the therapeutic compound of choice, the xanthophyll molecule provides a greater concentration of the medication within the macula than that achieved by the medication alone.

The compounds and methods of the present invention may be used to treat a wide variety of diseases of the eye. For example, diabetic retinopathy and the exudative form of AMD are characterized by neovascularization, in which the formation of abnormal blood vessels may lead to hemorrhage, retinal detachment and ultimately, legal blindness. Experimental evidence has implicated two molecules, vascular endothelial growth factor (VEGF) and protein kinase c, as key contributors to this process. Though conventional therapy emphasizes surgical intervention through laser photocoagulation, retinal cryotherapy, or photodynamic therapy, experimental, anti-angiogenic compounds, including drugs aimed at inhibiting VEGF and protein kinase c, have recently been developed and are now being tested in humans with encouraging results (Aiello, L. P., et al., *N. Engl. J. Med*, 1994, 331:1480; Aiello, L. P., et al., *Arch. Ophthalmol.*, 1995, 113: 1538-1544; Kliffen, M., et al., *Br. J. Ophthalmol.*, 1997, 81:154-62; Seo, M. S., et al., *Amer. J. Pathology*, 1999, 154: 1743-1753; Shih, S. C. et al., *J. Biol. Chem.*, 1999, 274: 15407-14; Yoshiji, H., et al., *Cancer Res.*, 1999, 59:4413-4418). Steroids are also being evaluated for the treatment of exudative AMD.

Thus, in an embodiment, the prodrug of the present invention comprises an anti-angiogenic agent conjugated to a xanthophyll carotenoid carrier. In an embodiment, the anti-angiogenic agent linked to the xanthophyll carrier comprises anecortave acetate, anti-VEGF aptamer (and other anti-VEGF agents), AMD-FAB, or protein kinase c inhibitor. Linking such agents to a xanthophyll carotenoid carrier such as lutein or zeaxanthin can increase retinal levels of these agents compared to the intravitreal or intraorbital delivery routes currently employed. In addition, xanthophyll-mediated drug delivery would avoid the complications associated with invasive methods.

In an embodiment, the compounds, compositions, and methods of the present invention are effective for the treatment of retinoblastoma. Chemotherapy is starting to replace external beam irradiation and enucleation as the primary therapy for retinoblastoma, with radiotherapy and enucleation reserved for disease recalcitrant to chemotherapy. For example, retinoblastoma may treated with monthly cycles of systemic chemotherapy using drugs such as carboplatin, etoposide and/or vincristine. Laser photocoagulation with hyperthermia (transpupillary thermotherapy) and/or retinal cryopexy may also be used as adjuvant therapies to chemoreduction. Although such procedures achieve a high survival rate, chemoreduction therapy routinely produces a variety of transient side effects, ranging from nausea and vomiting, to increased susceptibility to infectious diseases (Lumbroso, L., et al., *Ophthalmology*, 2002, 109:1130-1136). More significantly, the long-term side effects of chemotherapy in children afflicted with retinoblastoma, who are genetically susceptible to subsequent, non-ocular cancers, are unknown.

Thus, in an embodiment of the present invention, linking an anti-neoplastic drug to a xanthophyll carrier enables higher levels of the drug to be achieved in the retina with lower doses of the anti-neoplastic agent than currently used. Preferably, the anti-neoplastic agent comprises etoposide or vincristine, which are anti-neoplastic agents used to treat retinoblastoma. Other anti-neoplastic agents known in the art may also be used. This increased specificity associated with xanthophyll promoted delivery of the anti-neoplastic agent to the eye can minimize systemic side effects and lead to enhanced drug efficacy, improved visual outcomes, and a greater survival rate.

Additionally, retinal inflammation, arising from surgical manipulation, infection, trauma, or immune-mediated processes, is an eye disorder that may benefit from xanthophyll-linked medications. For example, cystoid macular edema (CME) is the collection of exudative fluid pockets within the layers of the retina. CME is a prevalent cause of visual loss following cataract extraction—a common surgery performed worldwide. Although the pathogenesis of CME remains uncertain, experimental and clinical evidence implicates prostaglandin-mediated inflammation. Prostaglandins are molecules derived from arachidonic acid, a phospholipid present in cell membranes. Once released, as for example due to the physiological response associated with surgical manipulation of the eye, prostaglandins can lead to increased microvascular permeability, breakdown of the blood-retinal barrier, and CME. Current first-line therapy for CME includes topical NSAIDs, which inhibit prostaglandin formation from arachidonic acid; or steroids, which directly block prostaglandin activity. In refractory cases, however, invasive delivery methods (such as retrobulbar injections) are used (Flach, A. J. et al., *Am. J. Ophthalmol.*, 1991, 112:514; Flach, A. J. et al., *Am. J. Ophthalmol.*, 1987, 103:479; Fung, W. E., *Ophthalmology*, 1985, 92:1102; Blair, N. P., et al., In Principles and Practice of Ophthalmology, W B Saunders, 2000, pp. 2080-2088; Guex-Crosier, Y., *Doc. Ophthalmol.*, 1999, 97:297-309; Pendergast, S. D. et al., *Am J. Ophthalmol.*, 1999, 128:317). Thus, in an embodiment, linking NSAIDs or steroids to a xanthophyll carrier may enable the effective prevention or treatment of CME in patients without resorting invasive means. Given the large number of cataract extractions performed annually, xanthophyll-mediated drug delivery has the potential to help thousands of patients.

Also, ocular pathogens may be treated with xanthophyll-linked antibiotics. For example, endophthalmitis is a blinding intraocular infection caused by bacterial or fungal organisms. Endophthalmitis may develop after penetrating eye trauma or as a complication of cataract and glaucoma surgery. Treatment for endophthalmitis has typically employed a regimen of intravenous antibiotics. However, evidence provided by the Endophthalmitis Vitrectomy Study revealed that systemic administration of antibiotics was ineffective—presumably because of poor ocular penetration (Doft, B. H., *Arch. Ophthalmol.*, 1991, 109:487). Instead, the study endorsed vitrectomy, an invasive surgical procedure, and intravitreal antibiotics.

Thus, in an embodiment, xanthophyll-mediated drug delivery may render invasive techniques unnecessary by systemically providing the therapeutic levels of antibiotic needed to treat the infection. Preferably, the antibiotic comprises ciprofloxacin. Other therapeutic agents known in the art to be effective against infectious pathogens may also be used. Thus, other therapeutic agents that may be used include, but are not limited to, antiviral agents and agents to prevent infection of the eye by protozoa, fungi or other microorganisms. In this way, xanthophyll-linked compounds specific for a variety of infectious retinopathies including, but not limited to, toxoplasmosis, histoplasmosis, and cytomegalovirus retinitis, may be developed.

Thus, the present invention describes that a variety of drug classes may display enhanced delivery to the retina through carotenoid carriers, potentially affecting the clinical outcomes of a wide range of ocular diseases. Using systemic administration route of carotenoid-linked drugs would avoid the complications associated with invasive techniques.

Development of Prodrugs for Delivery of Therapeutic Agents to the Retina

The present invention includes creating novel prodrugs that consist of a carotenoid carrier linked chemically to parent drugs with proven or experimental efficacy in the treatment of retinal and macular diseases. Similar methods and approaches are used to prepare prodrugs comprising appropriate carriers and therapeutic agents for the treatment of other diseases. A prodrug is a non-active molecule that releases an active principal (parent drug) at the desired site of action, improving the parent drug's pharmacokinetic properties, such as bioavailability and stability.

FIG. 1 shows the chemical structures of (3R,3'R,6'R)-lutein (Panel A) and (3R,3'R)-zeaxanthin (Panel B) which, in accordance with an embodiment of the present invention, comprise xanthophyll carotenoids that act as carriers to concentrate compounds in the eye. Other compounds, both xanthophyll-based and non-xanthophyll compounds, that are known to be concentrated in the eye may also be used. For example, xanthophyll derivatives or chemically modified xanthophyll compounds such as 3'-epilutein, meso-zeaxanthin, 3-hydroxy-beta,epsilon-caroten-3'-one, epsilon-lycopenes, or 5-Z-lycopenes may be used. Also, in an embodiment, carotenes may be used.

Figure 2A:
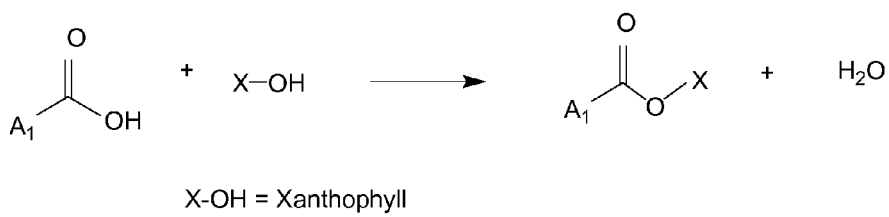
FIG. 2 shows a schematic illustrating the formation of prodrugs for concentrating therapeutics in the retina and macula of the eye having either a bipartate structure, with the therapeutic agent $A_1$ directly bound to the xanthophyll carrier (X—OH) (Panel A), or a tripartate structure, with the therapeutic agent $A_2$ bound to the xanthophyll carrier (X—OH) via an amino acid spacer (Panel B), in accordance with an embodiment of the present invention.

As described herein, the therapeutic agent of interest may be directly linked to the carotenoid carrier to form a bipartate structure. A schematic showing conjugation of a therapeutic agent ($A_1$-COOH) with a xanthophyll (X—OH) to form a bipartate prodrug of the present invention is shown in FIG. 2A. As shown in FIG. 2A, a therapeutic agent having a reactive (e.g., unblocked) carboxylic acid group ($A_1$-COOH) may be condensed with a xanthophyll (X—OH) in the presence of DCC (1,3-dicyclohexylcarbodiimide) to generate a prodrug having an ester bond forming a direct link between the xanthophyll carrier and the therapeutic agent. The bond linking the carrier to the therapeutic agent may be cleaved by cellular esterases. Depending upon the active group in the therapeutic agent, other direct bonds (e.g., carbon-carbon bonds; carbonate bonds, ether linkages) may be formed.

Figure 2B:
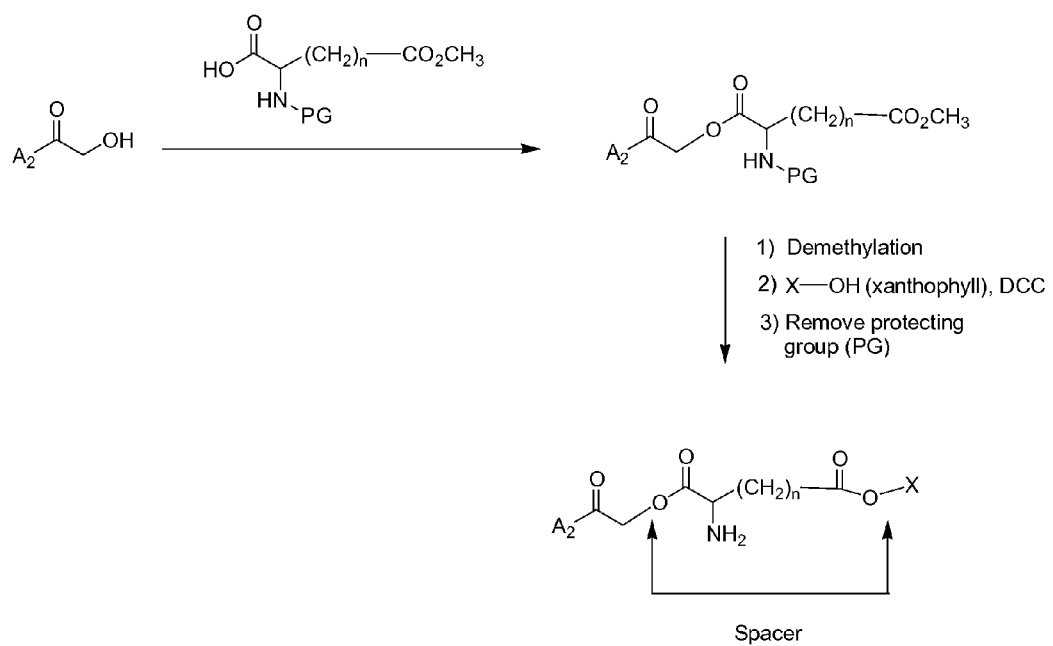

Alternatively, a spacer molecule may be used to link the therapeutic agent to the carotenoid carrier to form a tripartate structure. A schematic showing an embodiment of a tripartate prodrug of the present invention is shown in FIG. 2B. As shown in FIG. 2B, a therapeutic agent having a reactive (e.g., unblocked) hydroxyl group ($A_2COCH_2OH$) may be condensed with an amino acid ester (e.g. ω-methyl-N-carbobenzyloxy-aspartic or glutamic acid) (N-CBZ) in the presence of DCC to result in the formation of a direct bond between the therapeutic agent and the spacer upon loss of water. Next, a xanthophyll carrier (X—OH) is added by selective saponification and condensation (with loss of water) in the presence of DCC. Thus, the resulting prodrug comprises the therapeutic agent linked via an amino acid spacer to the xanthophyll.

The present invention describes the use of known and experimental therapeutic agents linked to carotenoid carriers for delivery to the eye. Therapeutic agents linked to carotenoid carriers may include the following: (1) etoposide (commercially available from Mylan Pharmaceuticals, Morgantown, W.V.) and vincristine, (Oncovin®; commercially available from Eli Lilly, Indianapolis, Ind.) both anti-neoplastic agents used to treat retinoblastoma; (2) ketorolac (commercially available from Roche Laboratories, Nutley, N.J.), an NSAID used to treat cystoid macular edema (CME) and posterior uveitis; (3) anecortave acetate (Alcon Inc., Forth Worth, Tex.), a putative anti-angiogenic steroid derivative for treatment of diseases that involve retinal neovascularization with concomitant visual loss such as exudative AMD, diabetic retinopathy (DR), and diabetic macular edema (DME); (4) the anti-VEGF aptamer pegaptanib (MACUGEN™ or EYE001, commercially available from EyeTech, Inc., New York, N.Y.), AMD-FAB (Rhu-Fab, a humanized antibody fragment; Genentech, San Francisco, Calif.), and protein kinase c inhibitor (Eli Lilly, Indianapolis, Ind.), three putative anti-angiogenic compounds that could also be used to treat exudative AMD, DR, and DME; (5) triamcinolone and fluocinolone (both commercially available from various suppliers), steroids used to treat such inflammatory disorders as posterior uveitis and CME, as well as exudative AMD, DR, or DME; and (6) ciprofloxacin (commercially available from Bayer Corporation, West Haven, Conn.), a fluoroquinolone antibiotic that can be used to treat a variety of ocular infections. Xanthophyll compounds may be obtained from Hoffmann-La Roche (Nutley, N.J.). The purity of all medications and xanthophyll carriers may be verified by high-performance liquid chromatography (HPLC). Table 1 describes at least some of the therapeutic agents which may used to generate the prodrugs of the present invention.

TABLE 1

Examples of prodrugs and their potential applications

| Prodrug | Drug Category | Chemical Structure of Therapeutic Agent | Potential Application(s) |
|---|---|---|---|
| lutein-etoposide, zeaxanthin-etoposide | anti-neoplastic agent | (etoposide structure) | retinoblastoma |
| lutein-vincristine, zeaxanthin-vincristine | anti-neoplastic agent | (vincristine structure · $H_2SO_4$) | retinoblastoma |
| lutein-ketorolac, zeaxanthin-ketorolac | NSAID* | (ketorolac tromethamine structure) | CME** |
| lutein-anecortave acetate, zeaxanthin-anecortave acetate | putative anti-angiogenic steroid derivative | (anecortave acetate structure) | exudative AMD, DR, DME*** |

TABLE 1-continued

Examples of prodrugs and their potential applications

| Prodrug | Drug Category | Chemical Structure of Therapeutic Agent | Potential Application(s) |
|---|---|---|---|
| lutein-protein kinase c inhibitor, zeaxanthin-protein kinase c inhibitor | putative anti-angiogenic compounds | (structure) | exudative AMD, DR, DME |
| lutein-triamcinolone, zeaxanthin-triamcinolone | steroid | [see Scheme 5, below] | posterior uveitis, CME, exudative AMD, DR, DME |
| lutein-fluocinolone, zeaxanthin-fluocinolone | steroid | (structure) | posterior uveitis, CME, exudative AMD, DR, DME |
| lutein-ciprofloxacin, zeaxanthin-ciprofloxacin | fluoroquinolone antibiotic | (structure) | endophthalmitis |

*NSAID = non-steroidal anti-inflammatory drug
**CME = cystoid macular edema
***AMD = age-related macular degeneration;
DR = diabetic retinopathy;
DME = diabetic macular edema In designing a prodrug, several factors are generally considered: Preferably, the prodrug is non-toxic and biologically inactive. Additionally, the prodrug should be resistant to serum enzymatic or chemical degradation. Also preferably, the prodrug has a lipophilic-hydrophilic balance and water solubility to ensure penetration of biological membranes. By selecting the appropriate natural carrier, the resulting prodrug is able to use specific, intermembrane transport mechanisms to be delivered to the tissue site required. Once inside the targeted tissue, the parent drug is released from the prodrug by enzymatic or chemical hydrolysis of the drug-carrier bond.

As described herein, bipartate and tripartate compounds may used in the design of prodrugs. In the bipartate approach, the drug and carrier (e.g., carotenoid) are directly bound. In the tripartate approach, the drug and carrier are connected by a spacer. The type of chemical bond, as well as the chemical properties of the spacer, can be used to control the stability and lipophilic-hydrophilic character of the prodrug (Cooperwood, J. S. et al., In Chemistry and Chemotherapy, C. K. Chu, ed., 2002, pp. 91-147).

To develop prodrugs comprising a xanthophyll carrier, several issues regarding the proposed drug-carrier systems must be addressed. First, lutein has two non-equivalent and stereoelectronically similar OH groups. Thus, selective monosubstitution is difficult because the reaction can yield a mixture of diastereomers. In contrast, zeaxanthin is a better candidate for monosubstitution because the C2 symmetry of zeaxanthin only produces only one isomer.

Also, depending on the nature of the therapeutic agent, disubstitution of the xanthophyll carrier may make the resulting compound too lipophilic and insoluble for adequate tissue adsorption and distribution to be achieved. In an embodiment, a number of hydroxyl (OH) or amine (NH$_2$) groups can be left free (or included in a spacer) to ensure a good lipophilic-hydrophilic balance. In general, however, disubstituted prodrugs are too insoluble for adequate absorption and distribution to be achieved.

Finally, since zeaxanthin is less likely to be deposited in such non-retinal tissues as fat (Toyoda, Y., et al., *Invest. Ophthalmol. Vis. Sci.* 2002; 43:1210-1221; Johnson, E. J., et al., *Am. J. Clin. Nutr.* 2000; 71:1555-62; Kaplan, L. A., et al., *Clin. Physiol. Biochem.*, 1990; 8:1-10), it may target the retina more effectively than lutein. The synthesis of a variety of prodrugs using zeaxanthin as a carrier is described in schemes 1-5 shown below. Analogous methods may be used for the preparation of prodrugs using other xanthophyll carriers.

Scheme 1. Zeaxanthin-Etoposide Prodrugs:

The anti-neoplastic agent etoposide is characterized by a polycyclic structure in which a vicinal diol and phenolic group can be functionalized. The acidity and reactivity of the phenolic group can be exploited to achieve stereoselectivity. However, the steric hindrance around these groups can influence reactivity in an unpredictable way, necessitating a spacer to connect the bulky drug and xanthophyll moieties.

The above scheme shows an example in which the etoposide diol is protected as acetonide and the phenolic hydroxyl is functionalized with an amino acid spacer. Subsequently, the etoposide-spacer compound is coupled, via a condensation reaction and loss of water, to zeaxanthin. Abbreviations used in the above scheme are as follows: PTSA=para-tolu-

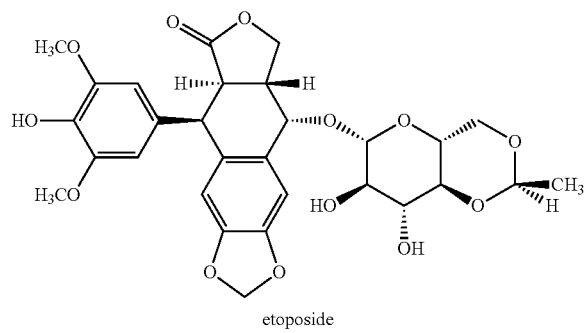

etoposide

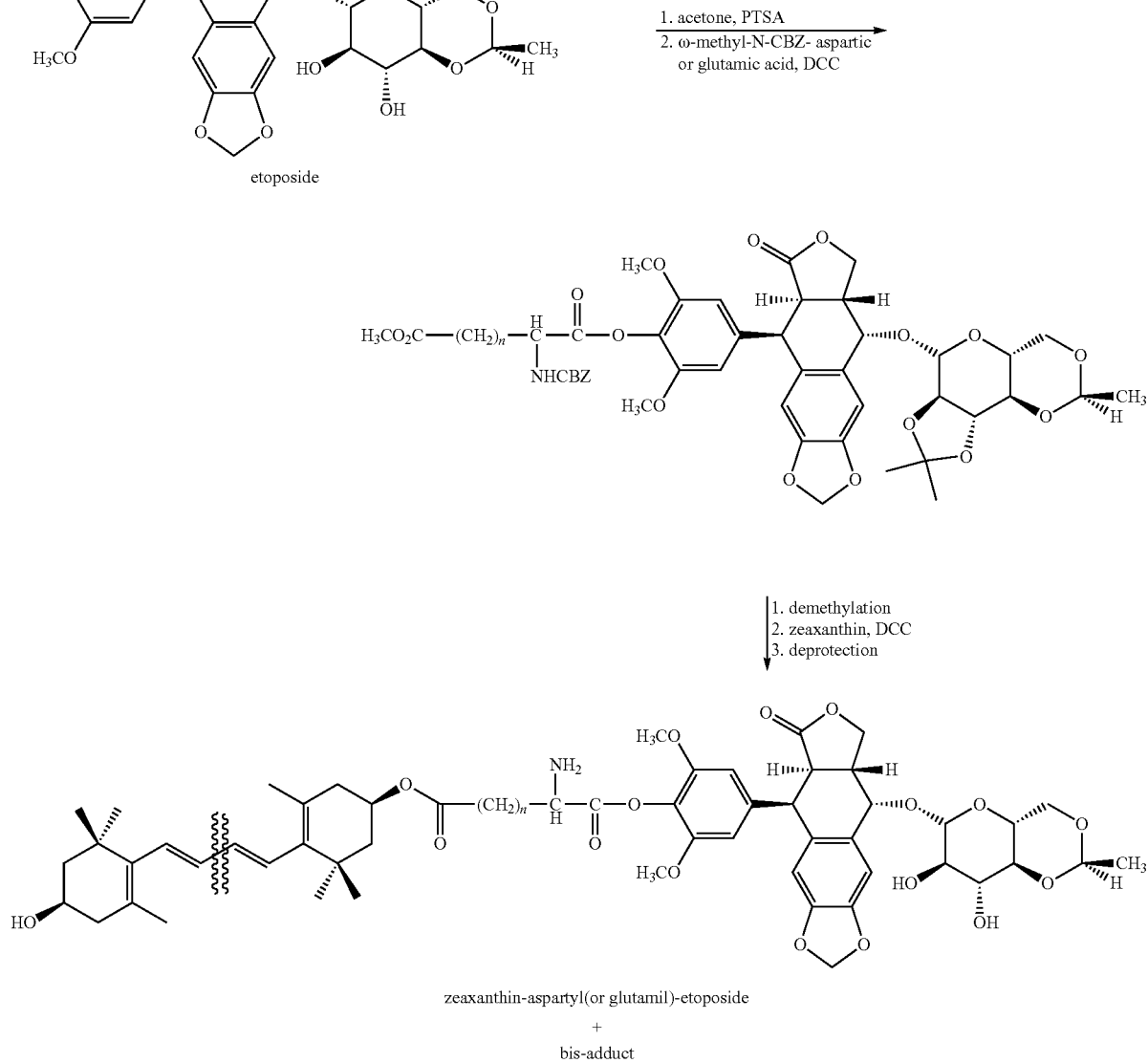

zeaxanthin-aspartyl(or glutamil)-etoposide
+
bis-adduct n = 0, 1 enesufonic acid; N-CBZ=N-carbobenzyloxy; and DCC=1,3-dicyclohexylcarbodiimide.

The use of amino acids as spacers is convenient because they are natural, non-toxic molecules and because their presence generally improves the hydrophilicity of the resulting prodrug. In addition, the use of different amino acids allows the synthesis of prodrugs with varying hydrophilicities and resistance to enzymatic degradation. In an embodiment, these aminoacyl prodrugs may release their parent drug through amidases and esterases.

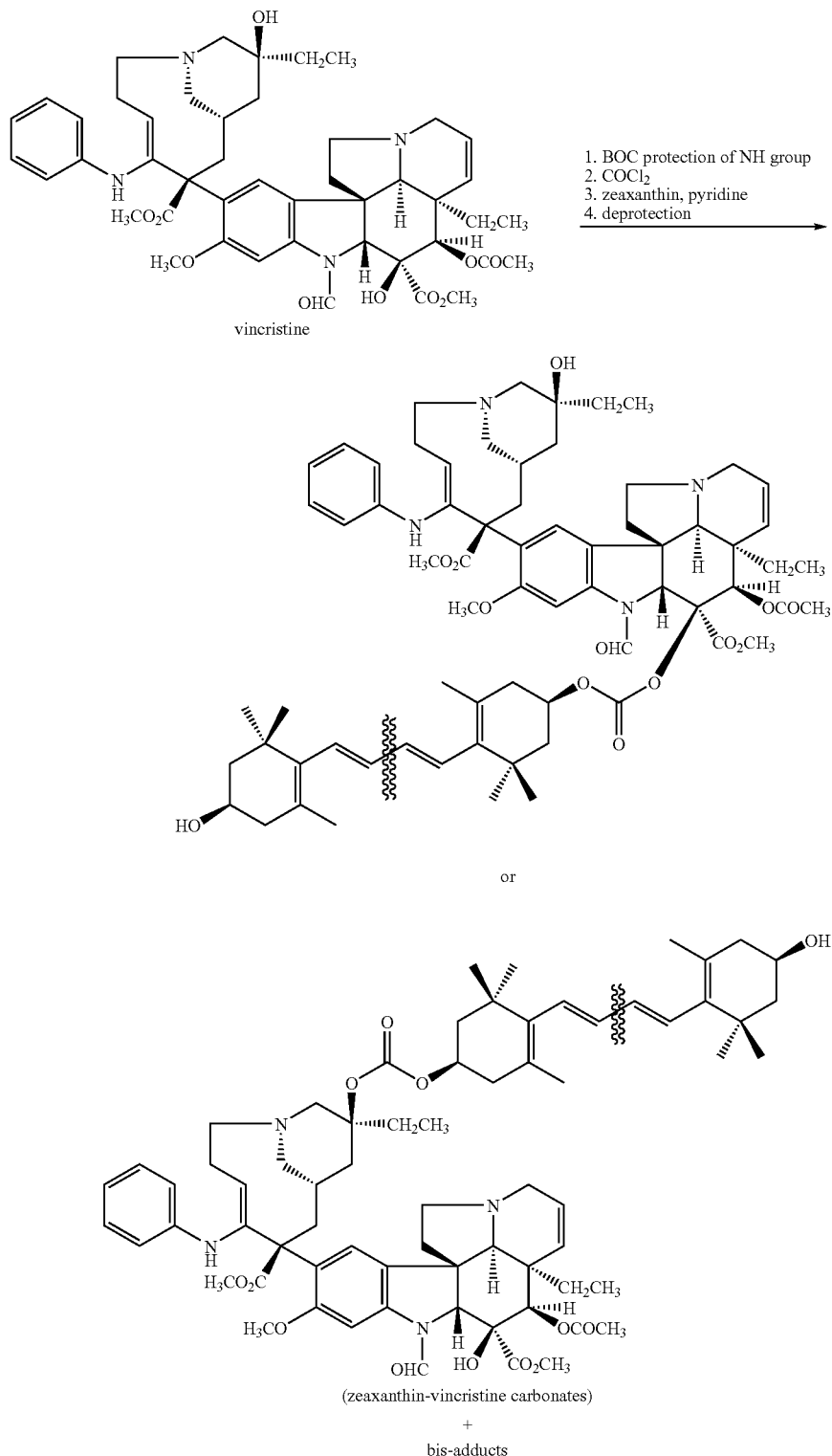

Scheme 2. Zeaxanthin-vincristine prodrugs: The anti-neoplastic agent vincristine is an alkaloid characterized by two quaternary groups and an indole ring. Prodrugs may be synthesized by functionalizing one of the two hydroxyl groups. The above scheme illustrates how zeaxanthin and vincristine can be coupled via a carbonate spacer. After blocking the amine group of vincristine, a bridging carbonyl group is added first to the hydroxyl group(s) of vincristine and then to the hydroxyl group of zeaxanthin by electrophilic substitution using oxalyl chloride ($COCl_2$). A carbonate spacer, which contains labile bonds, is appropriate because vincristine contains moieties that are potentially unstable. This prodrug is designed to release its parent drug through esterase-catalyzed hydrolysis. BOC is the t-butoxycarbonyl protecting group.

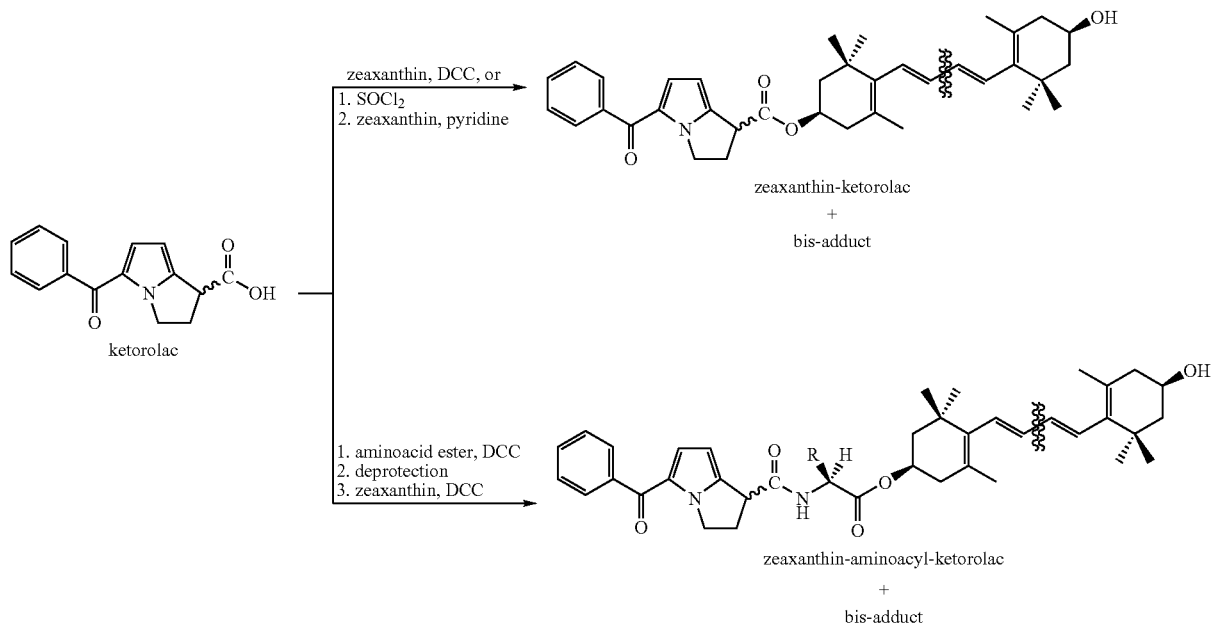

Scheme 3. Zeaxanthin-ketorolac prodrugs: Ketorolac is commercially available as the trimethamine salt. For the purpose of derivatization, the free acid can be used, although it is a racemate and will produce an inseparable, diastereomeric mixture when coupled directly to xanthophylls. The upper pathway of scheme 3 shows direct condensation between ketorolac and zeaxanthin, using either a dehydrating agent such as DCC, or via an acyl chloride intermediate. Both methods will give the mono- and disubstituted esters, however, careful control of reaction conditions should permit maximal yield of either product. In an embodiment, these ester prodrugs can release their parent drug through esterase-catalyzed hydrolysis.

The tripartate prodrug can also be synthesized, as illustrated in the lower pathway of the scheme, through condensation with an amino acid ester followed by selective saponification and coupling to zeaxanthin. These aminoacyl prodrugs should release their parent drug through amidases and esterases.

A.

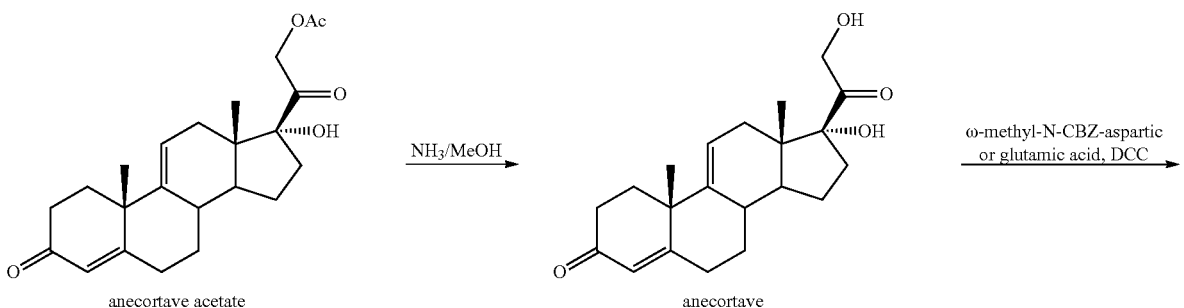

-continued
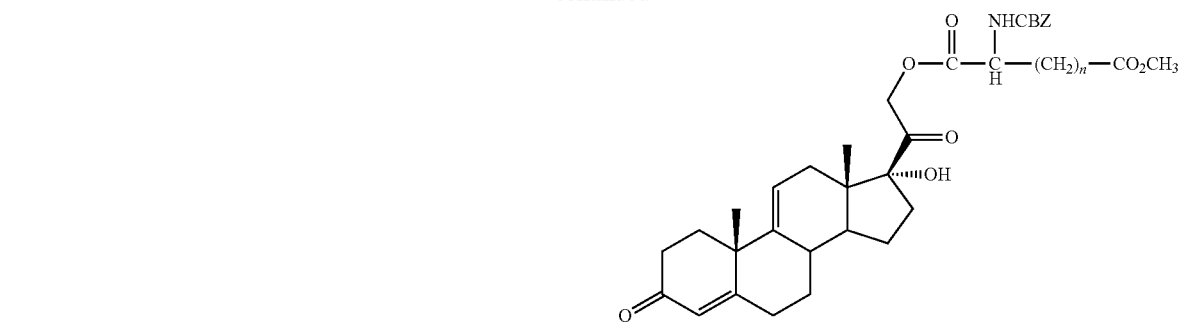
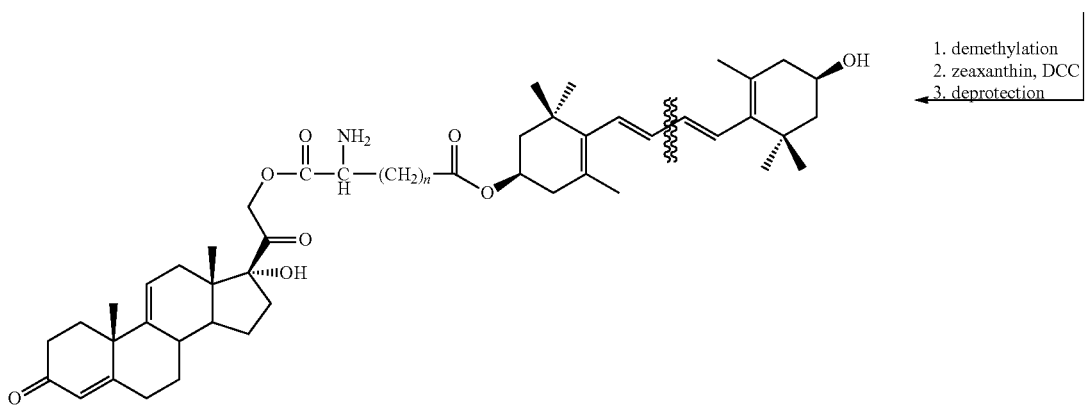
zeaxanthin-aspartyl(or glutamyl)-anecortave
+
bis-adduct
n = 0, 1
B.
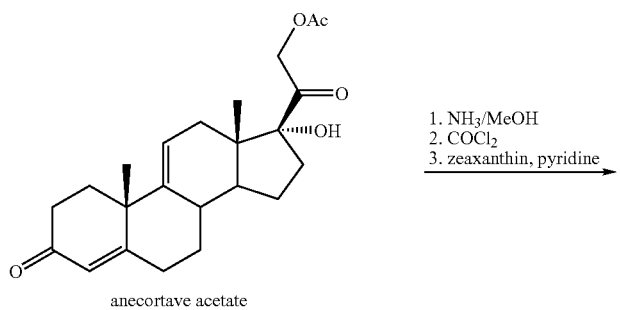
anecortave acetate

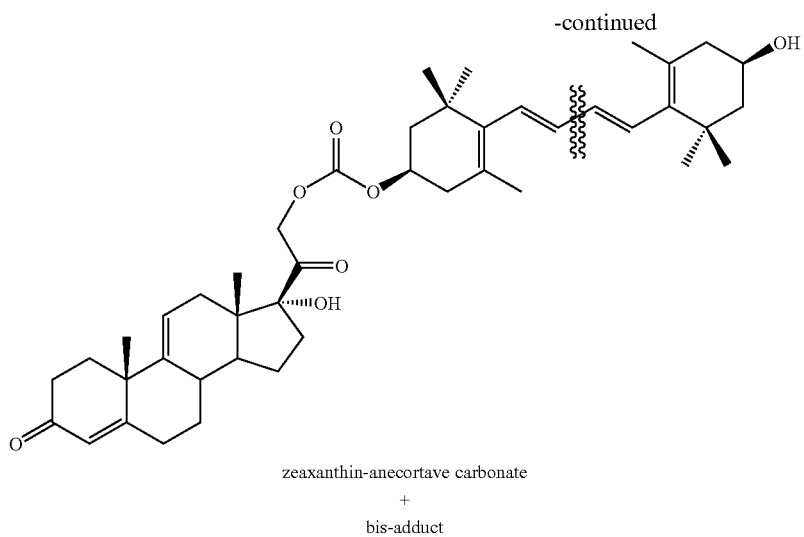

zeaxanthin-anecortave carbonate
+
bis-adduct

Scheme 4. Zeaxanthin-anecortave prodrugs: Anecortave is commercially available as an acetate. The acetate group is not essential for its activity, however, and may be substituted with a xanthophyll carrier. Although the xanthophyll carrier may be coupled to the secondary alcohol, substitution at the primary hydroxyl group should give a stable prodrug as the primary hydroxyl groups in both anecortave and the xanthophyll carrier are sterically hindered. To this end, a tripartate approach, in which the spacer is either a dicarboxylic amino acid (aspartic or glutamic acid) or a carbonate group, is appropriate. Scheme 4A shows formation of a zeaxanthin-amino acid-anecortave prodrug; in an embodiment, decomposition of this compound can be catalyzed by amidase enzymes. Scheme 4B shows formation of the zeaxanthin-anecortave prodrug with a carbonate spacer; in an embodiment, decomposition of this compound should be catalyzed by esterases.

A.

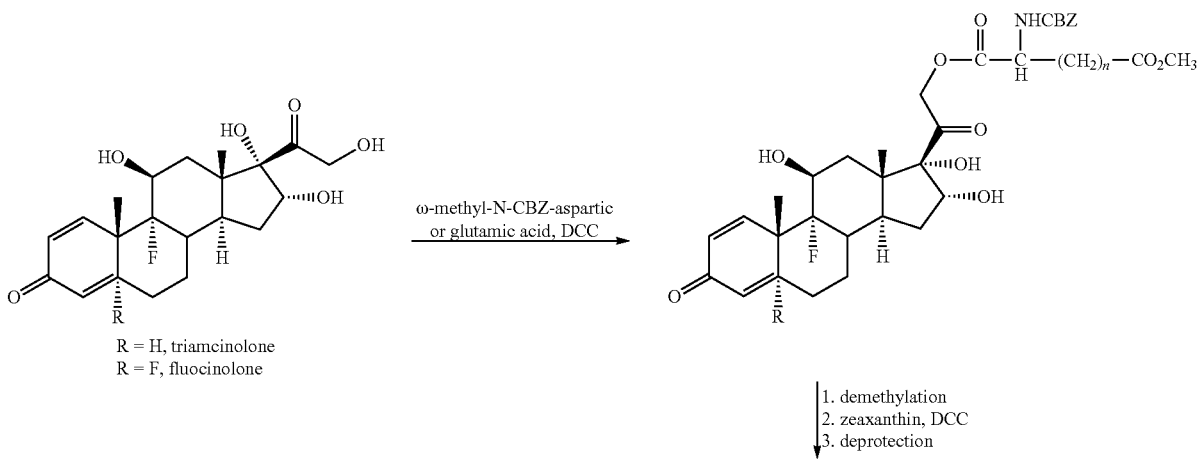

-continued

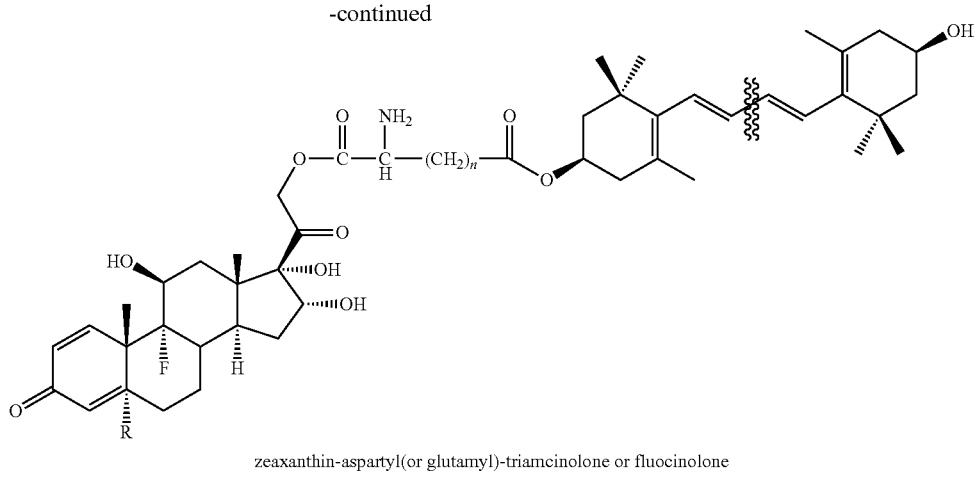

zeaxanthin-aspartyl(or glutamyl)-triamcinolone or fluocinolone
+
bis-adduct n = 0, 1

B.

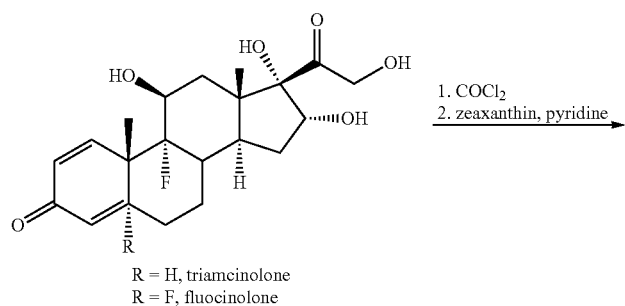

R = H, triamcinolone
R = F, fluocinolone

1. COCl$_2$
2. zeaxanthin, pyridine

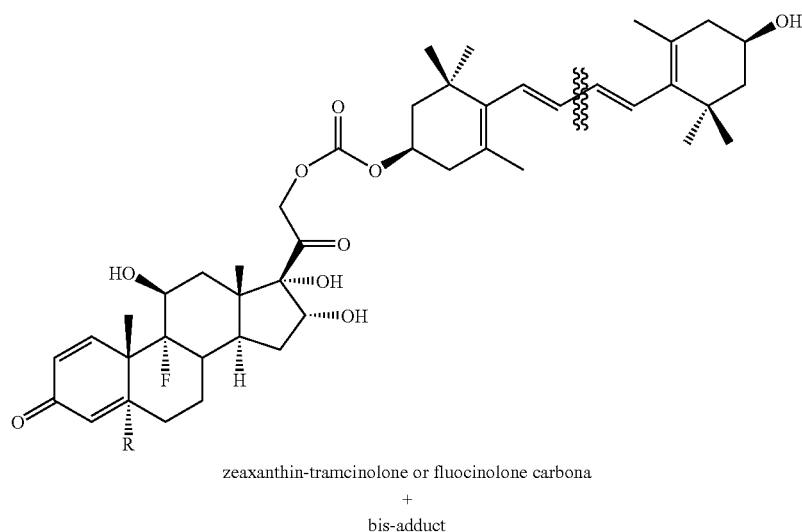

zeaxanthin-tramcinolone or fluocinolone carbona
+
bis-adduct

Scheme 5. Zeaxanthin-triamcinolone or fluocinolone prodrugs: Triamcinolone and fluocinolone are steroids that differ only in a fluorine substitution. Both of them are commercially available as acetonides or free polyalcohols. As in the case of anecortave, they can be coupled to xanthophylls via a dicarboxylic amino acid or carbonate spacer. These two approaches are shown in schemes 5A and 5B, above.

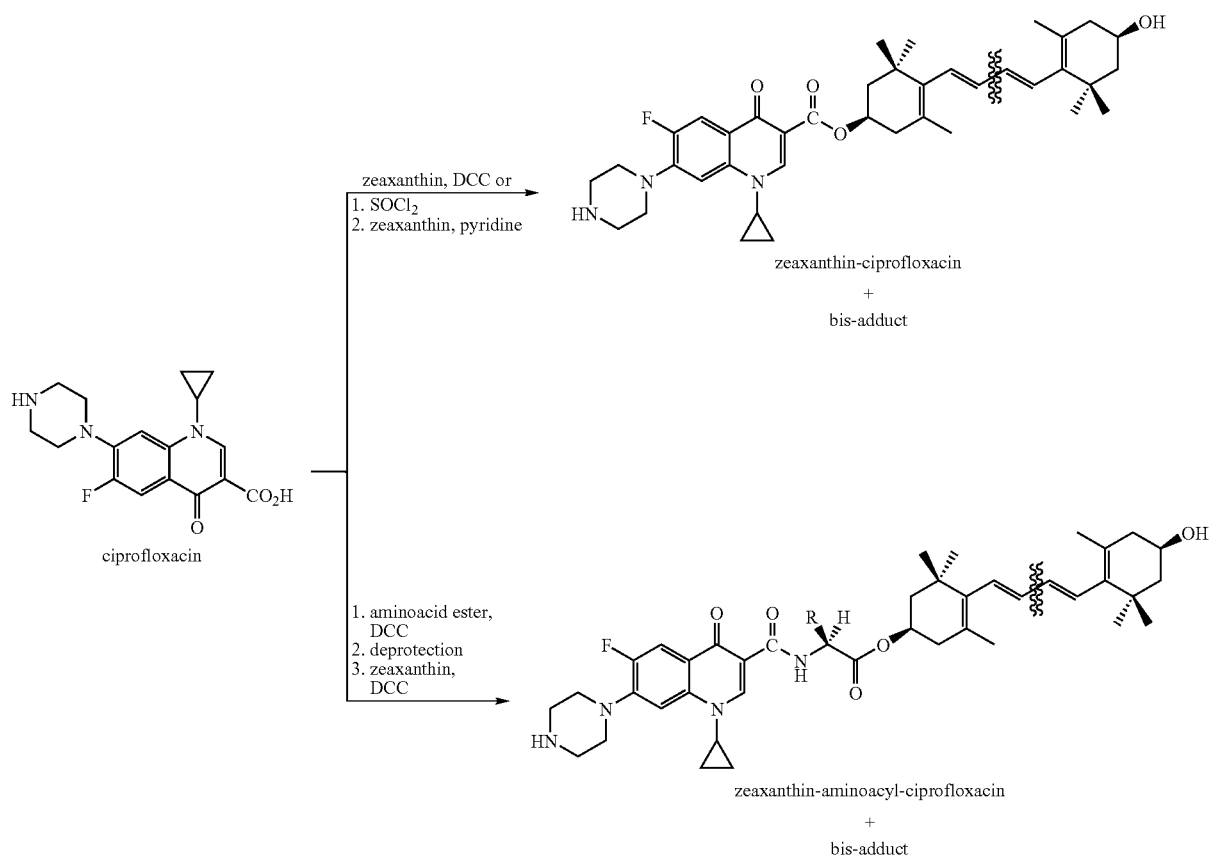

Scheme 6. Zeaxanthin-ciprofloxacin prodrugs: Ciprofloxacin is a fluoroquinolone antibiotic whose structure is characterized by carboxylic and secondary amino groups. The carboxylic group allows the creation of prodrugs through procedures outlined for ketorolac, above (Scheme 3). Thus, the above scheme shows the making of bipartate ester prodrugs in the upper scheme and tripartate prodrugs (with an amino acid spacer) in the lower scheme. Decomposition of these prodrugs is catalyzed by esterase and amidase enzymes, respectively.

After synthesis, prodrugs may be tested to characterize the stability of the carotenoid-parent drug bond. There are several animal systems which have been used as models to evaluate carotenoid metabolism. For example, studies related to xanthophyll metabolism and supplementation of the diet with xanthophylls have been carried out using frogs, rainbow trout, monkeys, and Japanese quail.

Thus, in an embodiment, prodrug stability may be evaluated using a quail liver homogenate. Livers of untreated quail may be surgically removed, ground, and mixed with saline solution and the prodrug of interest. A fraction of the resulting homogenate is extracted with acetonitrile, the supernatant dried with nitrogen gas, and a portion analyzed for prodrug, parent drug (e.g. therapeutic agent) and carotenoid levels by HPLC. Standard curves for both parent drug and prodrug stability are constructed using low, intermediate, and high concentrations of prodrug incubated in the liver homogenate for a range of times (e.g., 0.5 hrs up to 24 hours). Stability evaluation allows for development of prodrugs (through modification of the synthetic scheme) that are be stable enough to survive hematogenous transport to the retina while still remaining vulnerable to retinal hydrolytic enzymes.

Assessing Prodrug Delivery to the Target Tissue

In an embodiment, prodrugs may be evaluated to determine whether linking the therapeutic agent to a carotenoid carrier aids drug delivery to the tissue of interest (e.g., retina). For this purpose, 6 week old adult Japanese quail (*Coturnix japonica*), which have been shown to be a useful animal model in the study of carotenoid delivery to the retina, may be used (Toyoda, Y., et al., *Invest. Ophthalmol. Vis. Sci.,* 2002, 43:1210-1221).

i. Effect of a Xanthophyll-Deficient Diet on Prodrug Uptake

In an embodiment, an analysis is performed to determine whether a xanthophyll-deficient diet leads to depletion of retinal xanthophyll stores, and whether a wash-out period of xanthophyll depletion preceding exogenous xanthophyll supplementation increases prodrug uptake in the eye, or other tissue of interest.

For these studies, Japanese quail (Toyoda, Y., et al., *Invest. Ophthalmol. Vis. Sci.,* 2002, 43:1210-1221), or other model systems known by those of skill in the art, may be used. For example, in an embodiment, 6 week old quail are divided into 2 groups, each containing a predetermined number of quartets each having two male and two female animals. Group 1 receives a modified gamebird diet deficient in lutein and zeaxanthin (Purina Test Diet, Purina Mills, Richmond, Ind.) and Group 2 receives a standard gamebird diet, with each quartet being fed their respective diet for a predetermined time periods. For example, quartets A-G of each group may be fed their respective diets for 0, 1, 2, 4, 6, 8, and 12 weeks, respectively. The absence of xanthophylls within the modified food can be confirmed by HPLC.

At the conclusion of each time period, the quail are decapitated, and for quantitative analysis of xanthophylls in the retina, the eyes quickly enucleated and placed on ice. A circumferential incision may be made 2 to 3 mm anterior to the ocular equator, the anterior segment and lens is removed, and ice-cold phosphate buffer containing 50 µM EDTA is placed in the eyecup. Curved iridectomy scissors are used to cut and remove the vitreous close to the inner limiting membrane of the retina and, using intersecting cuts lateral to the pecten, the retina is peeled from the retinal pigment epithelium (RPE). Other tissue types may also be analyzed using biopsy techniques known in the art. All specimens, along with serum samples from each individual, are stored in darkness at −70° C. until analysis by HPLC (Toyoda, Y., et al., *Invest. Ophthalmol. Vis. Sci.*, 2002, 43:1210-1221).

For interpretation of the data, a statistical analysis comparing covariance of the heterogeneity of the slopes over time for the 2 groups (i.e., low and normal xanthophyll diet) is evaluated. If the slopes are not different, than a wash-out period with a xanthophyll-deficient diet is unnecessary. If the slopes are different, post hoc within time t-tests (adjusted for the multiple comparison) may be used to determine the time point at which the groups become different to define the appropriate wash-out period.

ii. Drug Delivery Route

Also, in an embodiment of the present invention, the preferred delivery route for the prodrug of interest may be determined. For example, in an embodiment, topical, intravenous, and intramuscular routes of administration are compared. The analysis also allows for an assessment of the efficacy of interstitial enzymes to hydrolyze the bond(s) between parent drug (i.e., therapeutic agent) and the carotenoid carrier. Additionally, the analysis may allow for assessment of any tissue necrosis that may result as part of the administration of the drug, such as necrosis resulting from the use of injection needles, subcutaneous pumps, or from the drug itself.

For this assessment, 6 week old quail may be divided into groups corresponding to the different modes of administration. For example, in an embodiment, there may be three test groups: (1) intravenous administration, (2) intramuscular administration, and (3) subcutaneous administration, with each group containing 2 quartets each having two male and two female birds, such that the first quartet of each group receives the parent drug (e.g., either ketorolac or triamcinolone) while the second quartet receives the corresponding prodrug (e.g., ketorolac linked to zeaxanthin). Subcutaneous administration of the drug may comprise the use of subcutaneous pumps (Alzet Osmotic Pumps; Durect Corporation, Cupertineo, Calif.). Dosages of parent drugs may range from about 2 mg/kg q.d. (e.g., ketorolac) to about 0.2 mg/kg q.d. (e.g., triamcinolone). Prodrug dosages are the molar equivalents of the drug doses.

The test subjects may receive either a xanthophyll-deficient diet or a standard diet as required to maximize xanthophyll uptake. After a predetermined time of prodrug/drug administration (e.g. 12 weeks for the quail assay), the animals are sacrificed, and serum and retinal tissue (and/or other tissue of interest) harvested for HPLC analysis of prodrug, drug, and xanthophyll levels. For data interpretation, a two-way analysis of variance may be used to determine differences (if any) between the different drug groups, the different modes of delivery, and any interaction between drug type and mode of delivery.

iii. Xanthophyll Levels in Retina

In another embodiment of the present invention, the time required for xanthophyll accumulation in the retina (or other tissue of interest) is determined. In an embodiment, 6 week old quail are divided into 2 groups, each containing 7 quartets each having two male and two female birds. Group 1 receives a lutein- and zeaxanthin-deficient diet while Group 2 receives a standard gamebird diet. After an optimum wash-out period, quartets A-G of each group receive a xanthophyll carrier (i.e., no therapeutic agent) using a preferred administration method (e.g., intravenous, subcutaneous, or intramuscular) and at a dosage equivalent to the molar quantity of the recommended dosage for the therapeutic agent of interest for increasing times (e.g, 0 day, 1 day, 1 week, 2 weeks, 4 weeks, 8 weeks, and 12 weeks).

At the conclusion of each time period, the test animals are sacrificed, serum, retina, and/or other tissue specimens collected, and tissue samples analyzed by HPLC for lutein and zeaxanthin content to determine the administration time necessary to produce measurable differences in xanthophyll levels for the tissue of interest. In an embodiment, the statistical analysis comprises an analysis of covariance of heterogeneity of the slopes across time for the two groups, with post hoc within time t-tests (adjusted for multiple comparisons) to determine when the difference occurs.

iv. Morbidity/Mortality Analysis

In an embodiment, the carotenoid conjugates of the present invention are evaluated for any potential toxicity. The therapeutic efficacy of endogenously active compounds can be determined by standard pharmaceutical procedures in cell culture or experimental animals using procedures known in the art. The dose ratio between toxic and therapeutic effects is the therapeutic index and may be expressed as $LD_{50}/ED_{50}$, wherein $LD_{50}$ is understood to represent the dose which is toxic to 50% of the subjects and $ED_{50}$ is understood to represent the dose which is effective in 50% of the subjects. Generally, compounds which exhibit large therapeutic indices are preferred.

For example, in an embodiment, toxicity is evaluated using the quail model. At age 6 weeks, quail may be divided into 2 groups, each containing 7 quartets (e.g. A-G) of two males and 2 females to test the toxicity of parent drugs and prodrugs. Both groups may receive a diet determined to maximize xanthophyll accumulation in the retina or other tissue of interest. For example, quartets A-G of Group 1 receive increasing amounts (e.g., 0.1×, 0.3×, 1×, 3×, 10×, 30×, and 100× of the recommended daily intravenous dose) of the therapeutic agent of interest (e.g., ketorolac or triamcinolone). Quartets A-G of Group 2 receives molar equivalent doses of the corresponding prodrugs (e.g., ketorolac linked to zeaxanthin). For example, in an embodiment, a recommended dose (1×) of ketorolac is 2 mg/kg q.d., and a recommended dose (1×) of triamcinolone is 0.2 mg/kg q.d. Morbidity is assessed by observing quail for behavioral changes, feather loss, the appearance of new lesions, etc. The lethal dose is defined as the point at which mortality is greater than, or equal to, a predetermined amount (e.g., 25%) of the individuals within a quartet. After the period of time required to maximize xanthophyll accumulation in the retina (or other tissue of interest), the quail are sacrificed, and tissue samples (e.g., serum and retina) may be analyzed by HPLC for parent drug, prodrug, and xanthophyll concentrations. Values obtained may be used to construct a dose-response curve, enabling selection of the optimal safe drug and prodrug dosage. Analysis of serum data will also allow a determination of the degree of prodrug hydrolysis prior to tissue deposition.

Analysis of ProDrug-Targeting

In another embodiment of the present invention, the ability of the prodrugs of the present invention to target the therapeutic agent to the retina and/or other tissue of interest is evaluated. For example, in these experiments six-week-old quail may be fed either a lutein- and zeaxanthin-deficient diet, or a regular diet as determined to maximize xanthophyll uptake in the retina. This period (i.e., the period during which the quail receive a xanthophyll-deficient diet without any drugs), is termed the "wash-out" period. After completion of a pre-set wash-out period, quail may be divided into 5 groups of four males and four females per group. Group C (control) receives sterile 0.9% saline, Group L (linked xanthophyll and drug) receives daily doses of the prodrugs of interest, Group D (parent drug alone) receives daily doses of the parent drug only, Group X (xanthophyll alone) receives daily doses of unlinked xanthophyll, and Group U (unlinked xanthophyll and unlinked drug) receives daily doses of unlinked xanthophyll and unlinked parent drug. For this evaluation, drugs and xanthophylls may be administered for a predetermined time period and using a method of administration determined to be optimal. Groups L, D, and U receive equivalent doses of medications. Groups X and U receive a dosage of xanthophyll carrier equal to the molar quantity of xanthophyll administered to Group L. To avoid any errors in group identification, each quail receives a color-coded leg band.

At the conclusion of the experimental period, quail are sacrificed and their retinas and other tissues of interest removed. Samples of retina, as well as serum, liver, and fat (i.e., tissues known to accumulate xanthophylls) (Toyoda, Y., et al., *Invest. Ophthalmol. Vis. Sci.,* 2002, 43:1210-1221), along with brain, heart, and kidney, are harvested to determine the specificity of drug targeting. Tissue samples may be analyzed by HPLC for xanthophyll, prodrug, and parent drug content. Table 2 summarizes the experimental groups used for drug targeting analysis.

TABLE 2

Xanthophyll-Drug Regimens and Measured Compounds

| Group | To Receive | Measured Compounds* |
|---|---|---|
| C (control) | 0.9% saline | xanthophyll, prodrug, and parent drug |
| L (linked xanthophyll and drug) | prodrug | xanthophyll, prodrug, and parent drug |
| D (conventional drug, alone) | conventional (parent) drug | xanthophyll, prodrug, and parent drug |
| X (xanthophyll, alone) | xanthophyll | xanthophyll, prodrug, and parent drug |
| U (unlinked xanthophyll and unlinked drug) | unlinked xanthophyll, unlinked drug | xanthophyll, prodrug, and parent drug |

*Measured compounds define the compounds to be assayed: for example, in the control, the measured prodrug (and presumably the parent drug) serves as a negative control, and the measured xanthophylls provides a measure of endogenous xanthophyll levels.

Dietary supplementation of zeaxanthin has been shown to produce a 4-fold increase in zeaxanthin concentration in quail fed a carotenoid-deficient diet (Toyoda, Y., et al., *Invest. Ophthalmol. Vis. Sci.,* 2002, 43:1210-1221). Although the absolute concentration differed between the two sexes, the magnitude of the increase was equivalent. Thus, for the prodrugs of the present invention, Groups L, X, and U should exhibit an increase in retinal xanthophyll concentration over xanthophyll control Groups C and D. Thus, in an embodiment, a sample size of 8 quail per group (4 male and 4 female) provides adequate power (power>80%) to detect differences of this magnitude when alpha=0.05.

For this analysis, the quantity of unaltered drugs and xanthophylls is the variable of interest. In order to determine xanthophyll and drug concentration differences between the different experimental groups, a one-way analysis of variance (ANOVA) can be performed within each region of measurement (retina, serum, liver, fat, brain, heart, and kidney). If the F-test for a group is significant, a series of preplanned contrasts to measure group differences of interest can then be used. The set of three orthogonal contrasts to determine differences in measured drug quantity is Groups L vs. D, Groups L vs. U, and Groups D vs. U. The set of 3 orthogonal contrasts to determine xanthophyll quantity differences is Groups L vs. X, Groups L vs. U, and Groups X vs. U. In addition, a Dunnett's test for all variables to establish differences between Groups L, D, X, and U and the placebo control group is used.

A multivariate analysis of variance (MANOVA) may be used to determine drug or xanthophyll concentration differences between the five groups (e.g., C, L, D, X, and U) and region of measurement, with adjustments for post hoc multiple comparisons of significant effects and investigate correlations of measurements between regions.

In addition, the normality of the drug and xanthophyll concentration measurements is assessed. If normality cannot be assumed, the analysis is performed on the rank or log transformed data or by appropriate nonparametric procedures. Results are reported as mean and SD for normal data or median and interquartile range for non-normal data.

Therapeutics

The invention contemplates methods of administration which are well known in the art. For example, in an embodiment, administration of the compound is systemic, as for example by parenteral administration, using intramuscular, subcutaneous, intravenous, or intra-arterial routes. In yet another embodiment, administration is topical to the eye, as for example using eye drops. In another embodiment, the method of administration is by a transdermal patch. Also, administration may employ a time-release capsule. In yet another embodiment, administration of the compound is oral or as an aerosol. In another embodiment, administration of the compound is sublingual.

Pharmaceutical formulations can be prepared by procedures known in the art. For example, the compounds can be formulated with common excipients, diluents, or carriers, and formed into tablets, capsules, suspensions, powders, and the like. Examples of diluents that are suitable for systemic administration include water, saline and/or buffered physiological solutions. Also, physiological preservatives (e.g., benzalkonium chloride), antibiotics, and compounds to adjust the osmolarity of the formulation of the solution may be included.

Other fillers and carriers which may also be employed, depending upon the method of uptake, include the following: fillers and extenders such as starch, sugars, mannitol, and silicic derivates; binding agents such as carboxymethyl cellulose and other cellulose derivatives, alginates, gelatin, and polyvinyl pyrrolidone; moisturizing agents such as glycerol; disintegrating agents such as agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

In an embodiment, the dose of prodrug comprises levels of the therapeutic agent of interest that are used pharmacologically in animals and humans. Also preferably, the dose of prodrug in a local concentration of therapeutic agent which ranges from 0.005 nM to 50 µM, and more preferably, from 0.05 nM to 1 µM, or even more preferably, from 1 nM to 100 nM.

Also, the ability of prodrug may a function of cell division and the length of the cell cycle. Thus, application of the prodrug may be hourly, daily, or over the course of weeks. Thus, preferably, the effective amount of the prodrug comprises from about 1 ng/kg body weight to about 200 mg/kg body weight. More preferably, the effective amount of the prodrug comprises from about 1 µg/kg body weight to about 50 mg/kg body weight. Even more preferably, the effective amount of the prodrug comprises from about 10 µg/kg body weight to about 10 mg/kg body weight. Alternatively, a continuous level of prodrug ranging from about 0.05-10,000 µg/kg/hour, or more preferably, 0.5-250 µg/kg/hr, or even more preferably 5-50 µg/kg/hour may be employed. The actual effective amount will be established by dose/response assays using methods standard in the art. Thus, as is known to those in the art, the effective amount will depend on bioavailability, bioactivity, and biodegradability of the compound.

It will be understood that each of the elements described above, or two or more together, may also find utility in applications differing from the types described. While the invention has been illustrated and described as methods and compositions for treatment of macular and retinal disease, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as described herein.

That which is claimed is:

1. A compound for the treatment of an eye disorder in a patient comprising a therapeutic agent chemically linked to a carotenoid, wherein said therapeutic agent is an anti-angiogenic compound selected from the group consisting of anecortave acetate, pegaptanib (EYE001), Rhu-fab and a protein kinase C inhibitor according to the chemical structure:

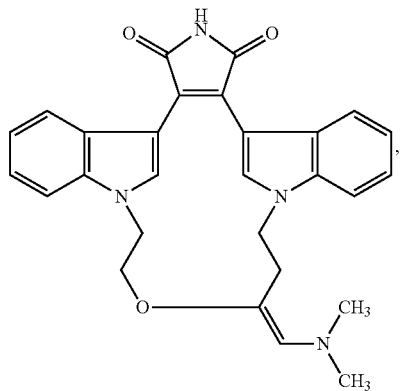

and wherein the carotenoid acts as a carrier to facilitate uptake of the therapeutic agent in the retina and or the macula.

2. The compound of claim 1, wherein the carotenoid comprises a xanthophyll.

3. The compound of claim 2, wherein the xanthophyll comprises zeaxanthin.

4. The compound of claim 1, wherein the linkage between the therapeutic agent and the carotenoid comprises a biologically cleavable bond.

5. The compound of claim 1, wherein a spacer molecule is used to link the therapeutic agent to the carotenoid.

6. The compound of claim 1, wherein the linkage between the therapeutic agent and the carotenoid comprises an amino acid spacer, a carbonate spacer, an ester bond, an amide bond, or a dicarboxylic acid bond.

7. The compound of claim 1 wherein said therapeutic agent is anecortave acetate.

8. The compound of claim 1 wherein said therapeutic agent is pegaptanib.

9. The compound of claim 1 wherein said therapeutic agent is Rhu-fab.

10. The compound of claim 1 wherein said therapeutic agent is a said protein kinase C inhibitor.

11. A composition for the treatment of an eye disorder in a patient comprising a pharmaceutically effective amount of a prodrug comprising a therapeutic agent linked to a carotenoid, wherein said therapeutic agent is an anti-angiogenic compound selected from the group consisting of anecortave acetate, pegaptanib (EYE001), Rhu-fab and a protein kinase C inhibitor compound according to the chemical structure:

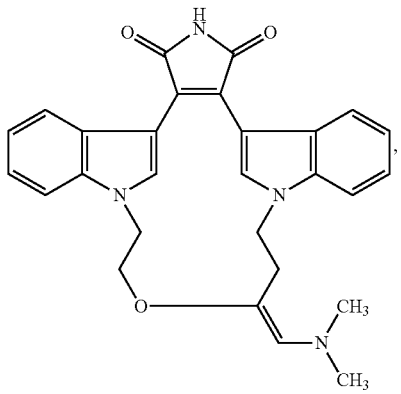

and a pharmaceutically acceptable carrier, wherein a pharmaceutically effective amount of the prodrug comprises an amount sufficient to ameliorate the eye disorder.

12. The composition of claim 11, wherein the carotenoid comprises a xanthophyll.

13. The composition of claim 11 wherein said therapeutic agent is anecortave acetate.

14. The composition of claim 11 wherein said therapeutic agent is pegaptanib.

15. The composition of claim 11 wherein said therapeutic agent is Rhu-fab.

16. The composition of claim 11 wherein said therapeutic agent is said protein kinase C inhibitor.

17. A kit for the treatment of an eye disorder in a patient comprising:

(a) a prodrug compound comprising a therapeutic agent linked to a carotenoid wherein said therapeutic agent is an anti-angiogenic agent selected from the group con sisting of anecortave acetate, pegaptanib (EYE001), Rhu-fab and a protein kinase C inhibitor according to the chemical structure:

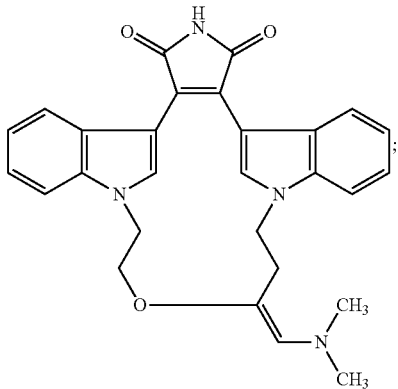

(b) a pharmaceutically acceptable carrier; and
(c) instructions to dispense a pharmaceutically effective amount of the prodrug in the pharmaceutically acceptable carrier to an individual in need thereof, wherein a pharmaceutically effective amount of the prodrug comprises an amount of sufficient to ameliorate an eye disorder in the individual.

18. The kit of claim 17, wherein the carotenoid comprises a xanthophyll.

19. The kit of claim 17 wherein said therapeutic agent is anecortave acetate.

20. The kit of claim 17 wherein said therapeutic agent is pegaptanib.

21. The kit of claim 17 wherein said therapeutic agent is Rhu-fab.

22. The kit of claim 17 wherein said therapeutic agent is said protein kinase C inhibitor.

* * * * *